US008948863B2

(12) United States Patent
Kraft et al.

(10) Patent No.: US 8,948,863 B2
(45) Date of Patent: Feb. 3, 2015

(54) PHOTOKINETIC OCULAR DRUG DELIVERY METHODS AND APPARATUS

(75) Inventors: Edward R. Kraft, Galveston, TX (US); Gabriela A. Kulp, Santa Fe, TX (US); Bernard F. Godley, Galveston, TX (US); Aristides P. Koutrouvelis, Galveston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 694 days.

(21) Appl. No.: 12/903,126

(22) Filed: Oct. 12, 2010

(65) Prior Publication Data

US 2011/0125076 A1 May 26, 2011

Related U.S. Application Data

(60) Provisional application No. 61/250,371, filed on Oct. 9, 2009, provisional application No. 61/328,625, filed on Apr. 27, 2010.

(51) Int. Cl.
*A61N 1/30* (2006.01)
*A61K 41/00* (2006.01)
(Continued)

(52) U.S. Cl.
CPC .............. *A61K 41/00* (2013.01); *A61F 9/0017* (2013.01); *A61N 5/062* (2013.01); *A61F 9/0079* (2013.01)
USPC .......................................................... 604/20

(58) Field of Classification Search
CPC ..... A61F 9/0017; A61F 9/0079; A61K 41/00; A61N 5/062
USPC ......... 604/20–22; 435/173.1; 607/53, 88, 141
See application file for complete search history.

(56) References Cited

U.S. PATENT DOCUMENTS 5,182,258 A 1/1993 Chiou
6,319,240 B1 * 11/2001 Beck .............................. 604/501
(Continued)

FOREIGN PATENT DOCUMENTS

WO 0151087 7/2001
WO 2004028421 4/2004
(Continued)

OTHER PUBLICATIONS

International Search Report and Written Opinion regarding corresponding PCT application No. PCT/US2010/052389, dated Nov. 29, 2011.
(Continued)

*Primary Examiner* — Kami A Bosworth
*Assistant Examiner* — Imani Hayman
(74) *Attorney, Agent, or Firm* — Wong Cabello Lutsch Rutherford & Brucculeri, LLP

(57) ABSTRACT

The present invention relates generally to transscleral, transcorneal, and transocular delivery of biologically active substances through the tissues, blood vessels and cellular membranes of the eyes of patients without causing damage to the cellular surface, tissue or membrane. The invention provides compositions and methods for enhanced transscleral, transcorneal and transocular delivery of biologically active substances using pulsed incoherent light, and particularly the transcleral, transcorneal or transocular delivery of high molecular weight biologically active substances to a patient using pulsed incoherent light. The invention further provides a device for the application of the pulsed incoherent light to cellular surfaces and membranes of the eye of a subject using those compositions and methods.

22 Claims, 13 Drawing Sheets

(51) Int. Cl.
*A61F 9/00* (2006.01)
*A61N 5/06* (2006.01)
*A61F 9/007* (2006.01)

(56) References Cited

U.S. PATENT DOCUMENTS

| | | | |
|---|---|---|---|
| 6,544,193 B2 * | 4/2003 | Abreu | 600/558 |
| 7,458,982 B2 | 12/2008 | Kraft et al. | |
| 7,854,753 B2 | 12/2010 | Kraft et al. | |
| 2004/0131687 A1 * | 7/2004 | Kraft et al. | 424/486 |
| 2008/0071252 A1 | 3/2008 | Santini et al. | |
| 2009/0047347 A1 | 2/2009 | Maggio | |
| 2011/0166500 A1 * | 7/2011 | Roy | 604/20 |

FOREIGN PATENT DOCUMENTS

| | | |
|---|---|---|
| WO | 2004032963 | 4/2004 |
| WO | 2005105155 | 11/2005 |
| WO | 2006138707 | 12/2006 |
| WO | 2008070479 | 6/2008 |
| WO | 2010105130 | 9/2010 |

OTHER PUBLICATIONS

H. Kim et al.; "Controlled Drug Release from an Ocular Implant: An Evaluation Using Dynamic Three-Dimensional Magnetic Resonance Imaging;" Investigative Ophthalmology & Visual Science; Aug. 2004; p. 2722-2731; vol. 45, No. 8; USA.

T. W. Olsen et al.; "Human Scleral Permiability: Effects of Age, Cryotherapy, Transsclera Diode Laser, and Surgical Thinning;" Investigative Ophthalmology & Visual Science; Aug. 1995; p. 1893-1903; vol. 36, No. 9; USA.

* cited by examiner

PHOTOKINETIC OCULAR DRUG DELIVERY METHODS AND APPARATUS

CROSS REFERENCE TO RELATED APPLICATIONS

This provisional patent application claims priority to U.S. Provisional Patent Application Ser. No. 61/250,371, filed Oct. 9, 2009, and U.S. Provisional Patent Application Ser. No. 61/328,625, filed Apr. 27, 2010, both of which are incorporated herein by reference in their entirety.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The inventions disclosed and taught herein relate generally to photokinetic delivery of biologically active substances across a mammalian ocular surface. More particularly, the invention provides methods, apparatus, and compositions for the transcleral/transcorneal, ocular delivery of biologically active substances, such as therapeutic agents, using pulsed incoherent light.

2. Description of the Related Art

Millions of people worldwide suffer from ocular diseases, many of which lead to visual impairment. Anterior segment diseases (dry eye, eye lid diseases) can be successfully treated with topical administration of drugs in eye-drop formulation. However, this minimally invasive technique only allows for less than about 5%, and many times less than 1%, of the administered drug to reach the drug target site before being washed away by tear formation or being absorbed systemically by the surrounding eye tissues. Eye drops may not be an effective method for administering larger molecular weight drugs into the eye for treatment of posterior segment eye diseases such as age-related macular degeneration, diabetic retinopathy, retinitis pigmentosa, and primary ocular lymphoma.

Systemic administration of an eye targeted drug has very poor bioavailability within the eye due to blood-ocular barriers that normally protect the eye from circulating antigens, inflammatory mediators, and pathogens. Typically, systemic administration does not yield therapeutic drug levels in the posterior vitreous, retina, or choroid, and although systemic administration can deliver drugs to the posterior eye, the large systemic doses necessary to achieve intraocular therapeutic levels are often associated with significant side effects.

As a result of these issues, direct intravitreal drug administration by needle injection is the current standard of care for many diseases of the eye. Recent drug formulation technologies have provided increased bioavailability and sustained release of drugs that are delivered by intravitreal needle injection. Even with drug formulation advancements, repeated invasive injections are required over extended periods of months and years. Intravitreal administration of drugs by needle injection is associated with an entirely new set of potentially catastrophic side effects such as infection, intravitreal hemorrhage or retinal detachment. Estimates in the literature range from 0.02% (Peyman, et al, *Retina*, Vol. 29(7), pp. 875-912 (2009)) to 0.2% (Jager, R. D., et al., *Invest. Ophthalmol. Vis. Sci.*, 45 (2004)) which would result in between 200 to 2,000 iatrogenic potentially blinding eye infections this year alone. Retinal detachment is estimated at 0.9% prevalence (Jager, 2004) from intravitreal injection, which translates to approximately 9,000 retinal detachments this year from this procedure. Additionally, ocular injections are painful and costly. Many disease states may require frequent drug administration directly into the eye to reach and maintain therapeutic levels. An effective, minimally invasive method of intraocular drug delivery is wanting. The proposed ocular drug delivery system overcomes the problems with repeated ocular needle injections and may be simple enough for home use.

It is widely recognized that stimulation of the optical sites of organic molecules result in conformational changes of the molecule which may produce a physical change in the shape of the molecule. When this stimulation is stopped the molecule would then return to a resting state and original physical shape. Also, if the stimulation is a low power, the relaxational time would be longer than if the molecule was stimulated with high optical power. The combination of low power and slow cyclical stimulation of the molecular optical sites would result in reversible conformational changes causing the molecule to bend and flex resulting in gross physical movement.

Passive transmembrane permeation is generally time and molecular weight (MW) dependent wherein larger molecules have less permeation flux rates than smaller molecules. While not intending to be bound by any theories, it is hypothesized that if a drug molecule in a pharmacologically acceptable formulation is placed on the surface of the sclera/cornea and cyclically illuminated with a selected wavelength of light at a selected pulse rate, the resulting cyclic physical shape change of the molecule may cause gross movement and result in the migration of the molecule across the sclera membrane. It is further hypothesized that narrow wavelength incoherent (non-laser) light from a light emitting diode (LED) source could be used for optical stimulation and that non-ionizing visible light with these characteristics would not be harmful to the drug molecule or the sclera itself. Applicants further hypothesize that the permeation with this system may be less molecular weight dependent than with passive transmembrane permeation methodologies.

The penetration of biologically active substances through the intraocular tissues occurs by either passive or active transport mechanisms, typically through the corneal and/or the non-corneal (conjunctival-scleral) pathways. Passive delivery or diffusion relies on a concentration density gradient between the drug at the outer surface and the inner surface of the biological barrier to be penetrated. The diffusion rate is proportional to the gradient and is modulated by a molecule's size, hydrophobicity, hydrophilicity and other physiochemical properties as well as the area of the absorptive surface. Typically, topically applied drugs reach the intraocular tissues by either the corneal and/or the non-corneal (conjunctiva-scleral) pathways, and efforts have been focused on either enhancing transcellular drug penetration by increasing drug lipophilicty through the use of prodrugs or analogs, or improving paracellular penetratioin by using enhancers to open tight junctions (Lee, et al., *J. Ocul. Pharmacol.*, Vol. 2, pp. 67-108 (1986)). However, it is common to see about 1% or less of an applied dose absorbed across the cornea and conjunctiva to reach the anterior segment of the eye (Lee, et al., in RETINA, 3$^{rd}$ Ed., Mosby, St. Louis, pp. 2270-2285 (2001)). Examples of passive delivery systems include ocularly-applied transdermal patches for controlled delivery of, for example, enkephalins, leupeptin (serine protease inhibitor), camostat mesylate (aminopeptidase inhibitor), nitroglycerine (angina), scopolamine (motion sickness), fentanyl (pain control), nicotine (smoking cessation), estrogen (hormone replacement therapy), testosterone (male hypogonadism), clonidine (hypertension), and lidocaine (topical anesthesia). The controlled delivery of these drugs can include the use of polymer matrices, reservoirs containing drugs with rate-controlling membranes and drug-in-adhesive systems.

In contrast, active delivery relies on ionization of the drug or other pharmacologically active substances and on means for propelling the charged ions through the tissue. The rate of active transport varies with the method used to increase movement and propulsion of ions, but typically this transport provides a faster delivery of biologically active substances than that of passive diffusion. Active transport delivery systems include methods such as subconjunctival ocular drug delivery, iontophoresis (transscleral and transscleral/conjunctival), and a variety of other routes which involve carrier-mediated drug transport systems.

Subconjunctival ocular drug delivery is an active transport method of attempting to elevate intraocular drug concentrations and minimize the frequency of dosing. Compared with direct intravitreal injection, this approach is less risky to the patient, and less invasive. Since the sclera is much more permeable than conjunctiva, the formidable permeability barrier consisting of both the cornea and the conjunctiva can be avoided all together with this approach. Advantages of subconjunctival ocular drug delivery, such as by the use of subconjunctival implants with nano-/microparticles and matrix materials, compared to subconjuctival injection of solution, is the achievement of higher drug concentrations and sustained release of the drug into both the vitreous humor and retinal areas (Gilbert, J. A., et al., *J. Control. Release*, Vol. 89, pp. 409-417 (2003)).

Iontophoresis is a technique used to guide one or more therapeutic ions in solution into the tissues and blood vessels of the body by means of a galvanic or direct electrical current supplied to wires that are connected to skin-interfacing electrodes. Although ionotophoresis provides a method for controlled drug delivery transdermally, irreversible skin damage can occur from galvanic and pH burns resulting from electrochemical reactions that occur at the electrode and skin interface. Consequently, its application to ocular therapies has been limited, with limited reports of its use in delivering molecules into the eyes of patients. For example, Asahara reported the use of transscleral iontophoresis to deliver 6-carboxyfluorescein-labeled phosphorothioate oligonucleotides and a 4.7 kb plasmid that expressed the green fluorescent protein (GFP) into albino rabbit eyes, with the nucleotides being detected in the anterior chamber, vitreous, and posterior retina with no alteration in length of the oligonucleotides (Asahara, et al., *Japn. J. Ophthalmol.*, Vol. 45, pp. 31-39 (2001)). More recently, a low-current, non-invasive iontophoretic treatment using dexamethasone-loaded hydrogels showed potential value in increasing the drug penetration to the anterior and posterior segments of the eye (see, Eljarrat-Binstock, E., et al., *J. Controlled Release*, pp. 386-390 (2005); and Myles, M. E., et al., *Advanced Drug Delivery Reviews*, Vol. 57, pp. 2063-2079 (2005)).

Other approaches to ocular drug delivery problems have included the use of ocular/ophthalmic inserts (e.g., OCUFIT SR®), collagen shields, vesicular systems, the use of liposomes and niosomes, the development of bioadhesives, mucoadhesive dosage forms, the use of lyophilisate carrier systems, and the use of nanoparticles and microparticles such as nanospheres made up of poly-d,l-lactic acid (PLA), polymethylmethacrylate (PMMA), cellulose, poly-ethyl-capro-lactone (PECL), or even chitosan (CS) nanoparticles (De-Campos, et al., *Pharm. Res.*, Vol. 21(5), p. 803 (2004)) as part of polymeric drug delivery systems for drug absorption in the eye. These approaches to drug delivery to the eye have been reviewed extensively in the medical literature (see, Das, S. & Suresh, P. K., *Int'l. J. Drug Delivery*, 2, pp. 12-21 (2010); and, Sultana, Y., et al., *Current Drug Delivery*, Vol. 3, pp. 207-217 (2006)). However, many of these approaches suffer limitations as well, such as being suitable only for delivering therapeutic molecules of a limited size (e.g., molecular weights of less than 200 Da), or unappealing side affects or potential for added eye damage for the patient seeking treatment.

Because of the inherent problems of the above-identified methods, a need exists for a safe and efficient transocular drug delivery method that eliminates side-effects and damage to the barrier function or appearance of the patient's eye caused by drug administration, and allows for a wide range of biologically active substances to be administered by such a method in therapeutically effective amounts. It would therefore be desirable to provide compositions, methods, and apparatuses to address these problems.

In vitro methods described within the present disclosure were developed to demonstrate the facilitated translocation of two separate compounds through sclera and corneal tissue using pulsed light. These in vitro studies, as described herein, suggest that the hypotheses proposed by the applicants been confirmed. The method of ocular drug delivery by pulsed incoherent light as described herein is referred to as "Photokinetic Ocular Drug Delivery" (PODD).

BRIEF SUMMARY OF THE INVENTION

The novel technology described herein generally relates to devices and methods for transscleral/transcorneal needleless drug administration. Specifically, the technology is an ocular drug delivery method wherein a drug applied to scleral/corneal tissue is illuminated with a selected narrow wavelength light from a LED source and pulsed at a selected frequency that then causes the drug to permeate into and through the tissue. The technology comprises in vitro methods for the selection of optical properties of light emitting devices applied to specific drug formulations thus defining in vivo administration systems. The technology provides a non-invasive method using light and drug reservoir devices to introduce drugs into the eye without the use of needles. The system is safer and less costly than ocular drug administration by needle injection.

In accordance with one aspect of the present disclosure, a method for the photokinetic transscleral ocular delivery of a biologically active substance to a subject is described, the method comprising preparing a solution comprising the biologically active substance and a solvent; applying the solution to a cellular surface of an eye of the subject; illuminating the solution on the cellular surface with a pulsed incoherent light having a selected wavelength, pulse rate and pulse duration or duty cycle; and allowing the solution to permeate through the cellular surface.

In accordance with a further aspect of the present disclosure, a device for photokinetic transscleral ocular drug delivery is described, the device comprising a generator that provides an oscillating electrical pulse; at least one light emitting diode that receives the oscillating electrical pulse and responds by providing an incoherent light; and, a drug reservoir cell that holds a solution comprising a high molecular weight biologically active substance and a solvent; wherein the drug reservoir cell is positioned to receive the incoherent light. In further accordance with this aspect of the disclosure, the generator is a electrical or repeat cycle square wave pulse generator. In further accordance with this aspect of the disclosure, the device includes a light pad having at least one light emitting diode (LED) embedded within it.

In accordance with another aspect of the present disclosure, an in-vitro method of photokinetic transscleral drug delivery to the eye of a subject is described, the method comprising preparing a solution comprising a biologically active substance and a solvent; applying the solution to an ocular cellular surface of a subject; illuminating the solution on the ocular cellular surface with a pulsed incoherent light having a selected wavelength, pulse rate and pulse duration with a device; and allowing the solution to permeate through the ocular cellular surface.

In further accordance with aspects of the present disclosure, methods for the transscleral delivery of one or more high molecular weight biologically active substances to the eye of a subject in need of such treatment is described, the method comprising preparing a solution comprising a high molecular weight biologically active substance and a solvent applying the solution to an ocular cellular surface of a subject; illuminating the solution on the ocular cellular surface with a pulsed incoherent light having a selected wavelength, pulse rate and pulse duration with a device; and allowing the solution to permeate through the ocular cellular surface. In further accordance with this aspect of the disclosure, the high molecular weight biologically active substance ranges in size from about 100 Da to greater than about 4500 kDa. In further aspects of the disclosure, the high molecular weight biologically active substance has a molecular weight of more than 1,000 Daltons, and in still further aspects, the high molecular weight biologically active substance has a molecular weight of more than 50,000 Daltons.

In accordance with yet another aspect of the present disclosure, a method for the treatment of a subject having a VEGF-related angiogenic disease affecting the eyes of the subject is described, the method comprising administering to a subject in need thereof a therapeutically effective amount of a biologically active substance using the transscleral/transcorneal PODD drug delivery methods described herein, wherein the VEGF-related angiogenic disease is selected from the group consisting of cancer, age-related macular degeneration (AMD), and diabetic retinopathy.

In accordance with a further aspect of the present disclosure, a process for treating an infection or disorder in a tissue of an eye of a subject is described, the process of which comprises transsclerally or transcorneally delivering a therapeutic composition to an eye using the photokinetic ocular drug delivery methods described herein, wherein the therapeutic composition comprises a biologically active substance having a molecular weight of at least 500 Daltons, a solvent, and optionally a gelling agent.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
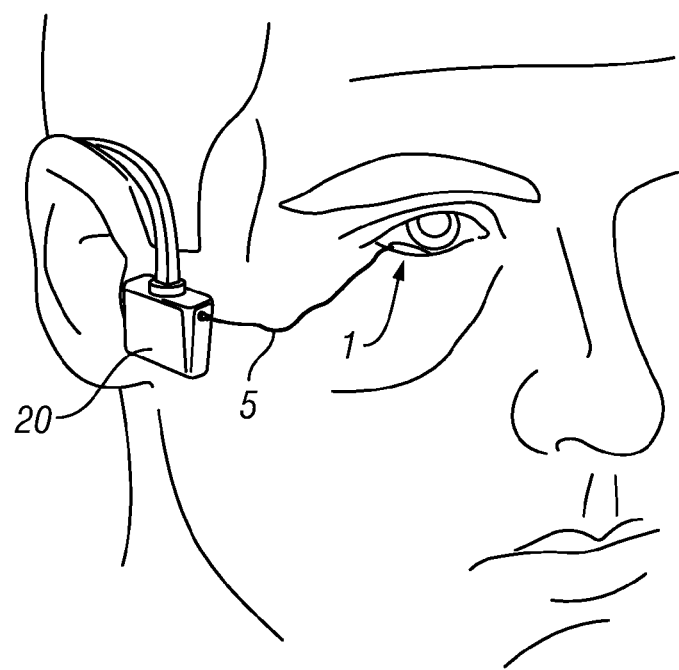
FIG. 1 illustrates an exemplary photokinetic transscleral drug delivery system in accordance with the present disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DEFINITIONS

The following definitions are provided in order to aid those skilled in the art in understanding the detailed description of the present invention. Units, prefixes, and symbols may be denoted in their SI accepted form. Unless otherwise indicated, nucleic acids are written left to right in 5' to 3' orientation, and amino acid sequences are written left to right in amino to carboxy orientation, respectively. Numeric ranges are inclusive of the numbers defining the range and include each integer within the defined range. Amino acids may be referred to herein by either their commonly known three letter symbols (e.g., Pro for proline), or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

The term "subject", as used herein, refers to any animal (i.e., vertebrates and invertebrates) including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

The term "biologically active substance" refers generally to any chemical, drug, antibiotic, peptide, hormone, protein, DNA, RNA and mixtures thereof that affects biological pathways or interacts with cellular components.

The term "chemical" denotes any naturally found or synthetically made small molecule or polymer. A chemical can be a polar (hydrophilic), non-polar (hydrophobic), oleophobic or oleophilic compound. Accordingly, the invention described herein is particularly useful for transport of compounds with of high molecular weight, which can be polar, non-polar, oleophobic, including fluorochemicals, and oleophilic, across at least the sclera of a patient.

The term "drug" denotes any natural or synthetic compound used for therapeutic treatment in mammals. Examples of drugs include, but are not limited to, anti-infective, antibiotic, antifungal, antineoplastics, anti-VEGF, antineovasculars, steroids, anti-inflammatory, immunomodulators, gas, antioxidants, nanoparticles, genes, cytokines, peptides, anti-thrombotics, nucleotides, RNAs, anti-compliment medications, compliment modulating medications, peptides, immunoglobulins, antibodies, antigens, anti-glaucoma medications, hormones, vitamins, silicone liquids, heavy liquid tamponades, cellular nutrients, anti-apoptotic agents, anticoagulants, tissue adhesives, cofactors, coenzymes, and enzymes. Specific FDA approved drugs which may be delivered by the PODD system described herein include, but are not limited to, triamcinolone acetonide (Kenalog; Bristol Myers Squibb, New York, N.Y.), pegaptanib (Macugen; OSI/Eyetech and Pfizer, New York, N.Y.), bevacizumab (Avastin; Genentech, San Francisco); and ranibizumab (Lucentis; Genentech). Numerous other agents available on an investigational basis such as VEGF trap (Regeneron; Tarrytown, N.Y.) may also be included.

Vitamins are organic chemicals that are essential for nutrition in mammals and are typically classified as fat-soluble or water-soluble. Vitamins required to maintain health in humans include, but are not limited to, vitamin A (retinol), precursor to vitamin A (carotene), vitamin $B_1$ (thiamin), vitamin $B_2$ (riboflavin), vitamin $B_3$ (nicotinic acid), vitamin B (pantothenic acid), vitamin C (ascorbic acid), vitamin D (calciferol), vitamin E (tocopherol), vitamin H (biotin) and vitamin K (napthoquinone derivatives).

The term "antibiotic" refers to any natural or synthetic substance that inhibits the growth of or destroys microorganisms in the treatment of infectious diseases. Although not an exhaustive list, examples of antibiotics include amoxycillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, teracycline, coxycycline, chloramphenicol and zithromycin.

The term "peptide" refers to a compound that contains 2 to 50 amino acids and/or imino acids connected to one another. The amino acids can be selected from the 20 naturally occurring amino acids. The twenty conventional amino acids and their abbreviations follow conventional usage. See, for example, Immunology—A Synthesis (2.sup.nd Edition, E. S. Golub and D. R. Gren, Eds., Sinauer Associates, Sunderland, Mass. (1991)), which is incorporated herein by reference. The amino acids can also be selected from non-natural amino acids such as those available from Sigma-Aldrich (St. Louis, Mo.), including but not limited to alicyclic amino acids, aromatic amino acids, β-amino acids, γ-amino acids, norleucine, ornithine, N-methyl amino acids, homo-amino acids, and derivatives of natural amino acids, such as 4-nitro-phenylalanine and xanthenyl-L-asaparagine. Although not an exhaustive list, examples of suitable peptides include glycine-tyrosine, valine-tyrosine-valine, tyrosine-glycine-glycine-phenylalanine-methionine, tyrosine-glycine-glycine-phenylalanine-leucine and aspartic acid-arginine-valine-tyrosine-isoleucine-histidine-proline-phenylalanine.

The term "hormone" refers to a substance that originates in an organ, gland, or part, which is conveyed through the blood to another part of the body, stimulating it by chemical action to increased functional activity or to increase secretion of another hormone. Although not an exhaustive list, examples of hormones include methionine enkephalin acetate, leucine enkephalin, angiotensin II acetate, β-estradiol, methyl testosterone, progesterone and insulin.

A polypeptide, as used herein, is defined as a chain of greater than 50 amino acids and/or imino acids connected to one another.

The term "protein", as used herein, refers to a large macromolecule composed of one or more polypeptide chains. The term "isolated protein" is a protein that by virtue of its origin or source of derivation (1) is not associated with naturally associated components that accompany it in its native state, (2) is free of other proteins from the same species (3) is expressed by a cell from a different species, or (4) does not occur in nature. Thus, a protein that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The terms DNA and RNA as referred to herein mean deoxyribonucleic acid and ribonucleic acid, respectively. The term "polynucleotide" means a polymeric form of nucleotides of at least 10 bases in length, either ribonucleotides or deoxynucleotides or a modified form of either type of nucleotide. The term includes single and double stranded forms.

"Gelling agents," according to the present disclosure, are compounds that can behave as reversible or non-reversible networks. Under certain conditions, a gelling agent can be placed in a solvent to form a viscous solution. Under other conditions, that same gelling agent can be placed in the same or different solvent to form a gel. The role of gelling agents according to the invention is to prevent evaporation loss of the biologically active substance in the appropriate solvent. Examples of gelling agents include, but are not limited to, hydroxyethyl cellulose, NATRASOL™, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols and tyloxapol.

The term "solvent" according to the present disclosure is any aqueous or organic solvent that can be combined with the biologically active agent to form a solution. In one embodiment, the aqueous solvent is water. In another embodiment, the solvent can be an aqueous solution of either ethyl lactate or propylene glycol, both of which act as permeation enhancers. Alternately, the term "solvent" can also mean an adhesive used to embed a biologically active substance, for example, in a patch. Solvent can also refer to a pharmaceutically-acceptable medium combined with the biologically active substance to be used in powder form.

The term "therapeutically effective amount", as used herein, refers to an amount of an antibody, polypeptide, or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

The phrase "pharmaceutically acceptable salt" as used herein is meant to refer to those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zunch, Switzerland: 2002). The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, flimarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

The phrase "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefore.

The phrase "pharmaceutically acceptable carrier, diluent or excipient" as used herein includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Treating" or "treatment" as used herein covers the treatment of the disease or condition of interest, e.g., tissue injury, in a mammal, preferably a human, having the disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, the term "%" when used without qualification (as with w/v, v/v, or w/w) means % weight-in-volume for solutions of solids in liquids (w/v), % weight-in-volume for solutions of gases in liquids (w/v), % volume-in-volume for solutions of liquids in liquids (v/v) and weight-in-weight for mixtures of solids and semisolids (w/w), such as described in Remington's Pharmaceutical Sciences [Troy, David B., Ed.; Lippincott, Williams and Wilkins; 21st Edition, (2005)].

The term "drug" as used in conjunction with the present disclosure means any compound which is biologically active, e.g., exhibits or is capable of exhibiting a therapeutic or prophylactic effect in vivo, or a biological effect in vitro.

The term "donor solution" or "delivery medium" comprises the biologically active substance itself or any mixture of this substance with a solvent, a gelling agent, a photocatalytic agent, a carrier or adjuvant, a skin-penetrating agent, a membrane-penetrating agent and combinations thereof. The biologically active substance, or alternately "active ingredient" does not have to be dissolved in a solvent but can be suspended or emulsified in a solvent. The donor solution or delivery medium can take the form of an aqueous or an organic liquid, a cream, a paste, a powder or a patch.

Although not an exhaustive list, examples illustrating the term "mammal" include human, ape, monkey, rat, pig, dog, rabbit, cat, cow, horse, mouse, and goat. Skin surfaces or membranes according to the invention refer to those of a human or other mammal.

The term "viscous solution" refers to a solution that has an increased resistance to flow.

The term "cellular surface" refers to an outer layer of the skin, a cell membrane, or tissue.

The term "transmembrane" refers to the penetration and movement of a biologically active substance from an extracellular environment to an intracellular environment.

The term "transocular", as used herein, refers to the penetration and movement of a biologically active substance from an external region of the eye of a subject to the interior region of the eye of the subject.

The term "incoherent light" refers to electromagnetic waves that are unorganized and propagate with different phases. The term "pulsed incoherent light" is any incoherent light having a discrete ON and OFF period.

In contrast, "coherent light" refers to all light rays that are in phase and oriented in the exact same direction to produce a concentrated beam of light. Lasers generate these types of rays and can penetrate through materials such as solid media, including metals (e.g., sheet metal).

The term "light emitting diode" or "(LED)" as used herein refers to a device that generally emits incoherent light when an electric voltage is applied across it. Most LEDs emit monochromatic light at a single wavelength that is out of phase with each other. According to the invention, most, if not all, types of LEDs can be used. For example, an LED having output range from red (approximately 700 nm) to blue-violet (approximately 350 nm) can be used. Similarly, infrared-emitting diodes (IRED) which emit infrared (IR) energy at 830 nm or longer can also be used.

The terms "optically clear medium" or "light pad" as used herein refer to materials that act as a filter to all wavelengths except those wavelengths emitted from a light source. In a preferred embodiment of the present disclosure, the light pad is comprised of clear poly(methyl methacrylate) or clear silicon rubber.

The term "reflective coating or layer" as used herein is a material that is coated on at least one surface of the light pad. Those skilled in the art will appreciate that the reflective layer can be a wavelength specific reflective coating (e.g., aluminum, ZnO, silver or any reflective paint).

The term "photokinetic" as used herein refers to a change in the rate of motion in response to light, as an increase or decrease in motility with a change in illumination.

DETAILED DESCRIPTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Computer programs for use with or by the embodiments disclosed herein may be written in an object oriented programming language, conventional procedural programming language, or lower-level code, such as assembly language and/or microcode. The program may be executed entirely on a single processor and/or across multiple processors, as a stand-alone software package or as part of another software package.

Applicants have created methods, apparatus, and systems for the transcleral/transcorneal ocular delivery of biologically active molecules and compositions to a mammal, using photokinetic delivery methods and assemblies.

One embodiment of the invention relates to compositions for photokinetic transcleral/transcorneal delivery, also referred to herein as Photokinetic Ocular Drug Delivery (PODD) of one or more biologically active substances to and through the tissues of a patient's eyes, using preferably pulsed incoherent light or, alternatively, regulated coherent light. The composition may comprise a biologically active substance as the delivery medium.

The composition may alternatively comprise a biologically active substance and a solvent. The percent of biologically active substance in solvent can be in the range of between 0.0001 to 99.9999% (w/v). Preferably, the biologically active substance is present in a concentration range of between about 0.01% to about 2% (w/v). More preferably, the biologically active substance is present in a concentration range of between about 0.1 mg/ml to about 10 mg/ml in the solvent or, alternatively, between about 0.01% to about 1% (w/v). Due to the high level of permeation achieved by the methods and devices described herein, low concentrations of a biologically active substance in solvent or in other compositions described herein can be used for efficient transcleral or transcorneal delivery.

The composition may instead comprise a biologically active substance, a gelling agent and a solvent. The percent gelling agent in a solution of biologically active substance can vary depending on the type of gelling agent used. For example, Klucel is typically used at 1% (w/v), Natrasol at 1.5% (w/v), Carbopol at 0.75% (w/v), and TEA at 0.25% (w/v).

The biologically active substance of the above compositions for use in transcleral or transcorneal administration to a subject for therapeutic purposes may be selected from the group consisting of chemicals, drugs, antibiotics, peptides, hormones, proteins, DNA, RNA and mixtures thereof. Preferably, in accordance with one aspect of the present disclosure, the biologically active substances which may be used for transcleral/transcorneal, non-invasive delivery to the eye of a subject are large molecules. As used herein, the phrase "large molecules" as applied to biologically active substances refers to those biological substances having molecular weights of at least 100 Daltons (Da), preferably more than about 500 Daltons (Da), more preferably more than about 1,000 Daltons (Da), and even more preferably a molecular weight of more than about 5,000 Daltons (Da), such as molecular weights of about 50,000 Daltons or greater, including compounds having molecular weights of about 100,000 Daltons (Da) or more, such as compounds having molecular weights of about 150,000 Daltons (Da), e.g., about 149 kDa in the case of infliximab (REMICADE®). For example, the biologically active substances which may be therapeutically administered to a subject using the PODD methods of the present disclosure may be large molecules having a molecular weight ranging from about 100 Da to about 150,000 Da, or ranging from about 500 Da to about 150,000 Da, as well as ranges within this range, such as from about 1,000 Da to about 130,000 Da, from about 5,000 Da to about 125,000 Da, and from about 10,000 Da to about 100,000 Da, as well as ranges within these ranges, such as from about 20,000 Da to about 135 Da, inclusive. In accordance with the present disclosure, as used herein, the molecular weight of a molecule refers to the sum of the weights of the atoms of which it is made, typically abbreviated as "MW" or "mw", and herein typically expressed in Daltons (Da).

The drug may be selected from the group consisting of anti-infectives, antibiotics, antifungals, antivirals, antineoplastics, anti-VEGFs, antineovasculars, steroids, anti-inflammatories (including NSAIDS), immunomodulators, gases, antioxidants, nanoparticles, genes, cytokines, peptides, antithrombotics, nucleotides, RNAs, anti-compliment medications, compliment modulating medications, peptides, immunoglobulins, antibodies, antigens, anti-glaucoma medications, hormones, vitamins (such as cyanocobalamin, vitamin $B_{12}$), amino acids, silicone liquids, heavy liquid tamponades, cellular nutrients, anti-apoptotic agents, anticoagulants, tissue adhesives, cofactors, coenzymes, and enzymes. In a preferred embodiment of the present disclosure, the drug is an anesthetic, preferably lidocaine.

The compositions according to the invention may also comprise antibiotics as the biologically active substance. Antibiotics according to the invention are selected from the group consisting of amoxycillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, teracycline, coxycycline, chloramphenicol, tobramycin, and zithromycin. In a preferred aspect of this embodiment, the biologically active substance is the antibiotic vancomycin.

The compositions according to the invention may also comprise antivirals as the biologically active substance. Antivirals according to the invention are selected from the group consisting of guanosine derivatives, nucleoside phosphonates, phosphonic acid derivatives, oligonucleotides, and combinations thereof, as well as pharmaceutically acceptable salts, solvates, hydrates, and derivatives thereof. In a preferred aspect of this embodiment of the present disclosure, the antiviral is foscarnet (FOSCAVIR™, Astra Zeneca), fomivirsen sodium (VITRAVENE™, Isis Pharmaceuticals), trifluridine (VIROPTIC™), ganciclovir, cidofovir, and vidarabine (Vira-A™, Monarch Pharmaceuticals).

Similarly, in another embodiment of the present disclosure, the biologically active substance is a peptide selected from the group consisting of known biologically active peptides, including but not limited to antibiotic peptides, antifungal peptides, anticancer peptides, immunological and inflammatory peptides, opioid peptides, neurotrophic peptides, and the like. In a preferred embodiment of the present disclosure, the peptide is insulin-like growth factor-1 (IGF-1; also known as somatomedin C or mechano growth factor and having a molecular weight of 7649 daltons).

In further embodiments of the present disclosure, the biologically active substance to be transsclerally delivered using the PODD system described herein is a hormone or steroid, or a pharmaceutically acceptable salt, solvate, hydrate, or derivative thereof. The hormones which may be used for therapeutic applications in accordance with this disclosure are selected from the group consisting of methionine enkephalin acetate, leucine enkephalin, angiotensin II acetate, β-estradiol, methyl testosterone, methyl prednisolone, corticosteroids (including corticosone, cortisone, hydrocortisone, and aldosterone), budenoside, progesterone, and insulin. In accordance with one particular aspect of this embodiment, the biologically active hormone is insulin. In accordance with another aspect of this embodiment, the biologically active substance is the steroid triamcinolone acetonide (TA; KENALOG™, Bristol Myers Squibb).

In another embodiment of the present disclosure, the biologically active substance to be transsclerally or transcorneally delivered to a subject using the PODD system described herein is a protein. The protein may be selected from the group consisting of enzymes, non-enzymes, antibodies (including monoclonal antibodies), and glycoproteins. In one embodiment of the invention, the protein is a humanized antibody. In accordance with yet another aspect of this embodiment of the present disclosure, the biologically active substance to be transclerally or transcorneally delivered to a subject is a fusion protein, such as VEGF Trap-Eye (an investigational drug manufactured by Regeneron, Tarrytown, N.Y.). In accordance with a further aspect of this embodiment of the present disclosure, the protein is a monoclonal antibody selected from the group consisting of adalimumab (Humira™; Abbott), bevacizumab (Avastin™; Genentech), daclizumab (Zenapax™; Roche); etanercept (Enbril™; Amgen); infliximab (Remicade™; Centocor); ranibizumab (LUCENTIS®; Genentech); and rituximab (Rituxican™; Genentech).

In another embodiment of the present disclosure, the biologically active substance to be transclerally or transcorneally delivered to a subject using the PODD system described herein is an anticancer agent such as 5-fluorouracil (5-FU), mitomycin C, melphalan, carboplatin, methotrexate, or colchicine, or a compound for the treatment of neovascular (wet) age-related macular degeneration (AMD), such as pegaptanib (MACUGEN™, OSI/Eyetech and Pfizer).

Compositions according to the present disclosure can also contain a gelling agent in combination with the biologically active agent and/or solvent. The gelling agent may be selected from the group consisting of hydroxyethyl cellulose, Natrasol™, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols, and tyloxapol. In a preferred embodiment of the present disclosure, the gelling agent is hydroxypropyl cellulose.

The compositions for therapeutic transscleral/transcorneal delivery using the methods and devices described herein may also comprise a solvent that is an aqueous solvent, an organic solvent, or a mixture thereof (such as oil-in-water microemulsions) as appropriate. In accordance with one embodiment, the aqueous solvent is water. In yet another embodiment, the aqueous solvent is an aqueous solution of ethyl lactate or propylene glycol. Preferably, the water is HPLC grade or purified by means such as reverse osmosis or distillation. In accordance with further embodiments of the disclosure, the solvent is an organic solvent selected from the group consisting of dimethylsulfoxide (DMSO) and poly(ethylene oxide)s (PEOs).

The donor solution or delivery medium according to the invention is comprised of a biologically active substance itself or any mixture of a biologically active substance with a solvent, a gelling agent, a carrier or adjuvant, a tissue-penetrating agent, emulsifier, one or more different biologically active substances, polymers, excipients, coatings and combinations thereof. In essence, the biologically active substance or substances can be combined with any combination of pharmaceutically acceptable components to be delivered to the cellular surface by the method described herein, e.g., photokinetic transscleral and/or transcorneal ocular delivery. The biologically active substance does not have to be dissolved in a solvent but can be suspended or emulsified in a solvent. The donor solution or delivery medium can take the form of an aqueous or an organic liquid, a cream, a paste, a powder, or a patch. The donor solution can also comprise microspheres or nanospheres of biologically active substances.

Figure 2:
FIG. 2 illustrates a close-up view of the system of FIG. 1, showing the photokinetic patch applied to the sclera under the eye lid.
Figure 3:
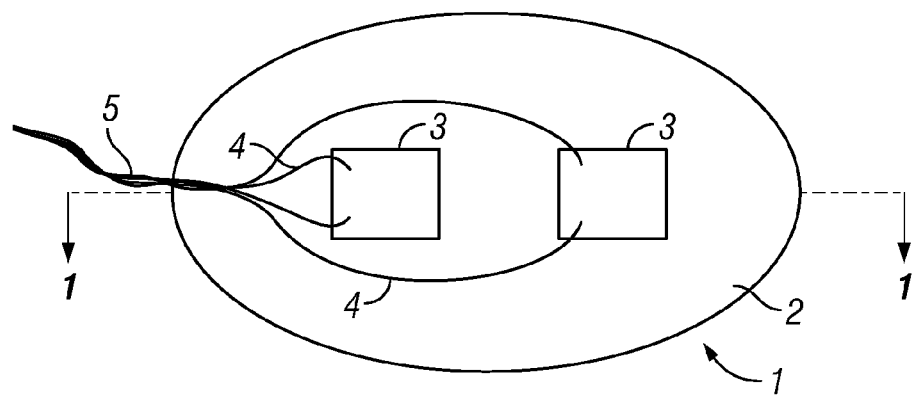
FIG. 3 illustrates a top view of the photokinetic eye patch of FIG. 1.
Figure 4:
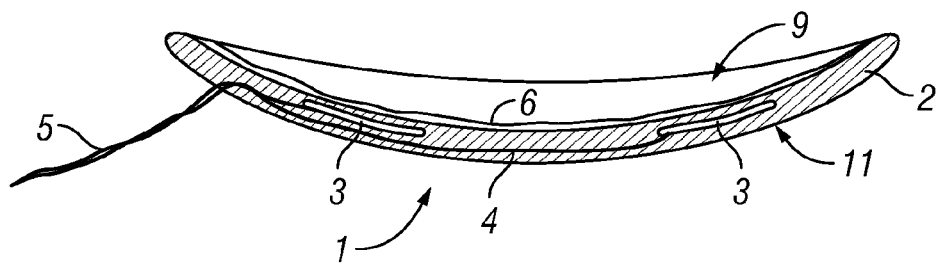
FIG. 4 illustrates a cross-sectional view through the patch of FIG. 1, taken along line A-A.
Figure 5:
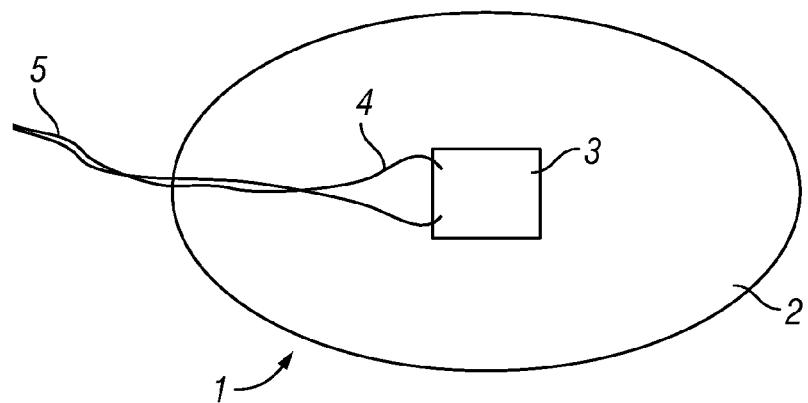
FIG. 5 illustrates an exemplary photokinetic eye patch with at least one LED embedded in the patch material.

Turning now to the Figures, FIG. 1 illustrates an intended application for a photokinetic transscleral and/or transcorneal drug delivery application in accordance with the present disclosure. FIG. 2 illustrates a closer view of the photokinetic patch of FIG. 1, showing the attachment of the patch to the sclera under the eyelid. FIG. 3 illustrates a top view of an exemplary photokinetic eye patch in accordance with the present disclosure. FIG. 4 illustrates a cross-section through the patch of FIG. 3. FIG. 5 illustrates an exemplary photokinetic eye patch in accordance with the present disclosure in combination with an LED embedded in the patch material These figures will be discussed in combination.

In FIG. 1, a general illustration of an intended application for photokinetic transscleral and/or transcorneal drug delivery in accordance with aspects of the present disclosure is shown, wherein a photokinetic transscleral drug delivery system is illustrated, comprising a patch, a square pulse generator, and a transmission wire connecting the two. The photokinetic patch 1 is applied to the exterior surface of the eye of a subject, in this case a human. An electronic pulse is generated by any suitable square wave pulse generator 20, which may be mounted over the ear or in other suitable manners (e.g., in a headband) proximate to the eye of the subject to be treated. This electrical pulse signal is transmitted to the photokinetic patch via an electric current transmitting wire 5. FIG. 2 illustrates an enlarged region of the subject's eye of the system of FIG. 1, showing the photokinetic patch 1 applied to the sclera 7 of the subject's eye, under the eyelid 8. The patch 1 includes a patch material, at least one LED associated with the patch, and electrical conducting wires 4. The patch material 2 may be any optically clear material that is flexible and soft enough to be applied to the eye without causing physical damage to the tissue. The patch is positioned so that the light output is directed in the direction of the eye tissue.

FIG. 3 illustrates a top view of the photokinetic eye patch 1 shown in FIGS. 1 and 2. As illustrated therein, the optically clear patch material 2 includes at least one LED 3 embedded within the patch material 2, although it is envisioned that the patch may include a plurality of LEDs, as appropriate. In the event that there are a plurality (two or more) LEDs 3 embedded in the material, the LEDs may be interconnected within the patch itself, and then connected to a lead wire 5 coming from the electrical square wave pulse generator 20. FIG. 4 illustrates a cross-sectional view of the patch 1 of FIG. 3 taken along line A-A. As is evident from this view, the patch is preferably manufactured with at least a slight curvature, so as to accommodate the normal curvature of the eye. Such curvature may be a predefined, standard curvature, or may be individually crafted for individual patients, depending upon their needs. As is also evident from FIG. 4, the LEDs 3 are embedded within the patch, and are electrically connected via communication wire 4, and are in turn connected to a conductor lead wire 5 coming from the wave pulse generator. The side of the patch 9 that contacts the eye, and which is opposite the exterior face 11 of the patch, in accordance with aspects of the present disclosure, is coated with a drug layer 6 in such a manner that the drug within the drug layer 6 comes into contact with the surface of the subject's eye. This drug layer 6 is preferably positioned between the eye tissue and the LED 3, so that the drug layer 6 receives the light generated by the LED during operation of the apparatus, so as to allow the drug within the layer 6 to transsclerally permeate the eye for therapeutic purposes.

FIG. 5 illustrates an alternative arrangement of the system of FIG. 1, wherein the photokinetic eye patch 1 includes at least one LED 3 embedded within the patch material 2, with electrical conducting wires 4 electrically attached to a wire in communication with the pulse generator 5.

Figure 6:
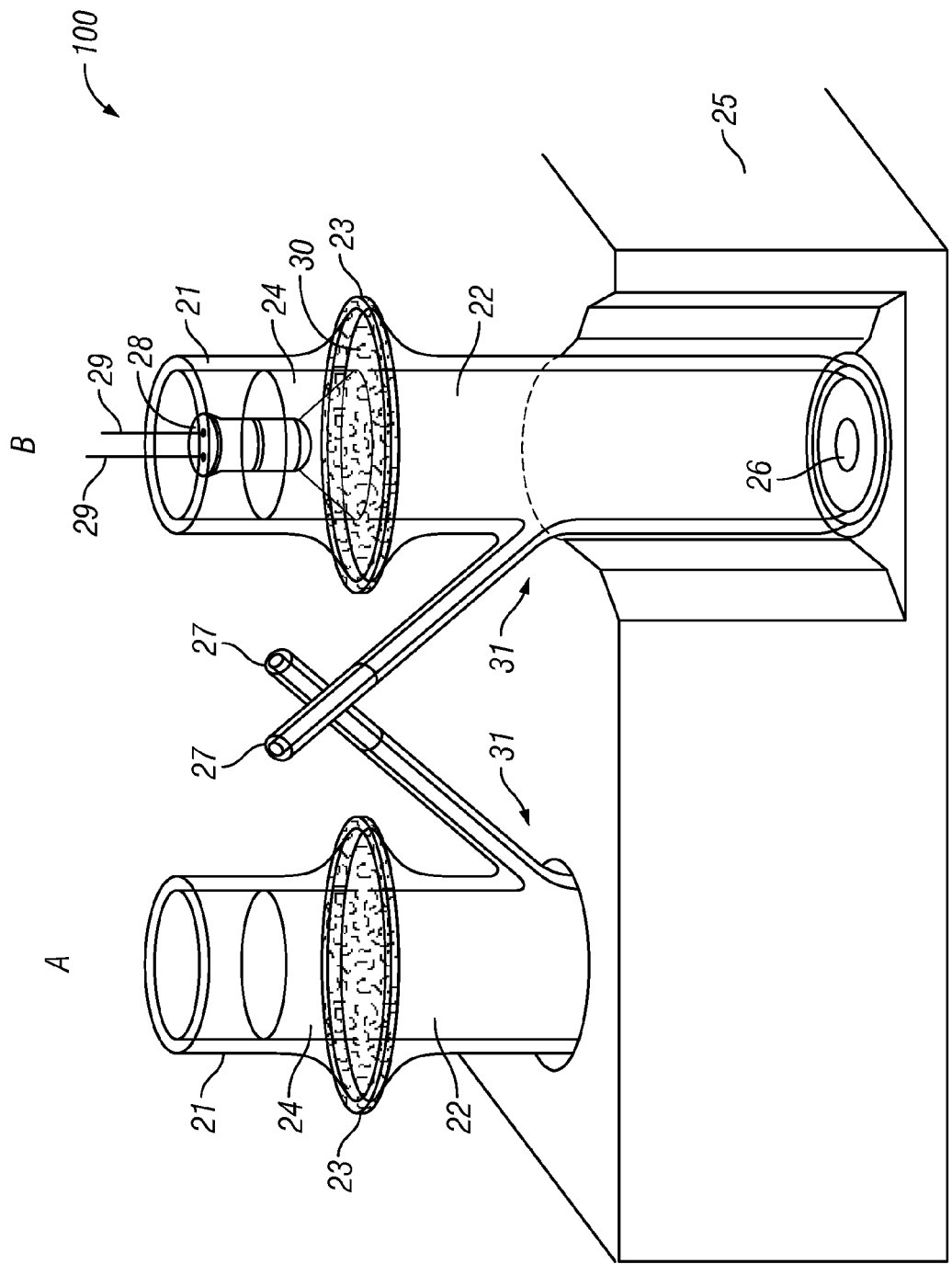
FIG. 6 illustrates exemplary Franz diffusion cell apparatus for in vitro determination of photokinetic conditions of light wavelength and pulse rate.

FIG. 6 illustrates an exemplary Franz diffusion cell apparatus for in vitro determination of photokinetic conditions of light wavelength and pulse rate, in accordance with the present disclosure. Franz diffusion cells 31 are shown within a heat block 25, one (B) being shown in partial cut-away for purposes of clarity.

The testing device illustrated in FIG. 6, in accordance with the present disclosure, provides photokinetic transscleral and transocular delivery of biologically active substances to a portion of an eye by illuminating a biologically active substance with pulsed incoherent light. Testing device can include a light source (not shown) that illuminates a biologically active substance in donor chamber 21 such that the biologically active substance diffuses into the eye tissue 23 with little to no damage to the eye tissue 23. Testing device can also be arranged such that the light source illuminating a biologically active substance in donor chamber 21 is horizontal or parallel to a surface on which it is mounted.

Testing device may include an electrical driver circuit that provides control signals to the light source such that pulsed incoherent light is provided to the donor chamber 21. The driver circuit may also provide control signals that control the intensity, direction, and/or frequency of the light source. A pulsed incoherent light advantageously and cyclically illuminates the subject drug formulation 24 producing a period of excitation and relaxation of the drug 24 and the eye tissue 23 which provides photokinetic transscleral and transocular translocation of biologically active substances within donor cell 21 into and through the eye tissue 23.

Electronic Driver circuit may regulate an electrical signal that turns (i.e., switches) light source ON and OFF at a particular frequency. Such an electrical signal may be provided, for example, by a voltage generator controlled by an electronic flasher circuit. Alternatively, a driver circuit may itself be a voltage generator and may produce an electrical signal to control the switching characteristics of light source. For example, a voltage generator coupled to light source may provide an electrical square wave to power the light source. This square wave may have a desired ON and OFF period such that light source provides pulsed incoherent light with a desired pulse frequency (e.g., a square wave period of 0.5 seconds ON and a 0.5 seconds OFF would cause light source to switch at 1 Hz or 1 cycle per second (CPS)).

The light source preferably provides incoherent light (to reduce the possible damage done to eye tissue 23 or cause damage to the drug 24 during the use of testing device). The light source may be, for example, an LED, halogen light source, fluorescent light source, natural light, or other source of light. More particularly, the light source can be a light emitting diode (LED) (fluorescence, 350-1700 nm) or an infrared light emitting diode (ILED) or a Mercury-Argon (253-922 nm), pulsed xenon (UV-VIS, 200-1000 nm), deuterium (UV, 200-400 nm), deuterium/halogen (UV/VIS/NIR, 200-1700 nm) or tungsten halogen (color/VIS/NIR, 360-1700 nm) light source. The light source preferably is operable in the range from red (approximately 700 nm) to blue-violet (approximately 350 nm). Similarly, infrared-emitting diodes (IREDs) that emit infrared energy at 830 nm or longer may be used.

The light source does not have to be an incoherent light source. In accordance with aspects of the present disclosure, the light source may be a coherent light source such as, for example, a laser. In that case, the driver circuit, or other regulation circuitry, is preferably used to turn the coherent light source ON and OFF to reduce the amount of damage to eye tissue 23 while still photokinetically delivering a biologically active substance 24 from the donor cell 21 into the eye tissue 23. Furthermore, a light regulation/conversion device may be placed between a coherent light source in the donor cell 21 to convert the coherent light to incoherent light.

Note that a device such as an electronic driver circuit or a controlled voltage generator is not required to pulse light source. Alternatively, a mechanical shutter may be employed between light source and donor cell. Such a shutter selectively OPENs and CLOSEs such that donor cell is supplied pulsed incoherent light from light source. The speed at which the shutter OPENs and CLOSEs determines the frequency of the light pulsed onto the eye tissue. Filters (not shown) may also be placed between light source and the donor cell in order to remove, for example, light of specific wavelengths that may damage the eye tissue or reduce photokinetic activity. Alternatively, the light source may not need be immersed or optically coupled with the drug solution found in donor cell. The essential arrangement is when a drug in contact with the subject's eye tissue is positioned to receive pulsed incoherent light from a selected source at a selected pulse frequency.

Preferably, the wavelength of light reaching eye tissue is chosen not only to reduce damage to the tissue, but also to increase the photokinetic activity in donor cell (e.g., 350 nm to 450 nm). The pulse rate of such light may also be between 1.7 cycles per second (cps) and 120 cps (e.g., 24 cps). If fluorescent light is employed as light source, it preferably has a wavelength range from about 260 nm to about 760 nm. If ultraviolet, visible, near infrared, or halogen light is employed as light source, the light source preferably has a wavelength range from about 340 nm to about 900 nm. The invention is not limited to these wavelengths. Any method to pulse illuminate the drug that is in contact with the eye tissue may provide the photokinetic transocular drug delivery.

Donor chamber 21 holds a biologically active substance (e.g., chemicals, drugs, antibiotics, peptides, hormones, proteins, DNA, RNA and mixtures thereof). Donor chamber 21 may also include a solvent that forms a solution with the biologically active substance. The solution may also include a gelling agent, as appropriate. The solvent may be an aqueous or an organic solvent. Furthermore, eye tissue 23 may be a cellular surface which is any layer of an eye, such as sclera, cornea or other eye tissue of a mammal. Generally, eye tissue 23 may be any medium that allows at least the biologically active portion drug formulation 24 contained in the donor chamber 21 to diffuse into that medium in response to that medium being exposed to selected a light source pulsed at a selected pulse rate. In one embodiment, this medium is a sclera for transscleral delivery. In another embodiment the medium is corneal tissue for transcorneal delivery.

A clamp (not shown) may optionally be included in testing device to couple donor chamber 21 and eye tissue 23 to the recipient chamber 22. Drug components comprising the donor formulation 24 placed in donor chamber 21 may be present in recipient chamber 22 as a result of the diffusion of at least the biologically active portion 24 of donor chamber 21 through eye tissue 23. Also, recipient chamber 22 may contain a solvent, e.g., HPLC grade water, wherein diffusion of at least the biologically active portion 24 of donor cell 21 through eye tissue 23 enters into the solvent. Generally, the concentration of the biologically active substance is higher in donor chamber 21 than in recipient chamber 22.

Temperature control device 25, such as a heat block, is preferably applied to at least a portion of the recipient chamber 22. Temperature directors may be included as a part of heat block 25 or coupled to the recipient chamber 22 to direct temperature control device 25. Temperature directors (not shown) may also be used to structurally provide support for a heat source such as a heat bath. For example, warm water may be placed in housing defined by temperature directors and a portion of recipient chamber 22 between temperature directors. Further to this example, a heat source may be used to heat such water. Alternatively, a heat source may be directly coupled to recipient chamber 22. Preferably, temperature control device 25 heats the Franz cell assembly 31 to a constant level. While the temperature of the solvent in recipient chamber 22 can vary, it is preferably about 37° C., human body temperature, or about 35.5° C., human eye surface temperature. For applications requiring Franz cell assembly 31 to be cooled, temperature control device 25 may additionally or alternatively be a cooling source. A temperature sensor (not shown) may be placed in, on, or about the Franz cell 31 or a heat source such that temperature control device 25 keeps the Franz cell 31 at a particular temperature for a particular period of time.

With continued reference to FIG. 6, stir bar 26 may be included in recipient chamber 22 to stir any solution in recipient chamber 22. Preferably, stir bar 26 constantly stirs the solution in recipient chamber 22. Recipient chamber 22 may be alternatively stirred, for example, by a shaking device. Removal of stir bar 26 would, for example, recipient chamber 22 to be easily sanitized while reducing the design complexity of recipient chamber 22 assembly. Stir bar 26 may be connected to an electrical motor (not shown).

Side arm port 27 may be included in recipient chamber 22 to add or remove samples to or from recipient chamber 22 or solutions to or from recipient chamber 22. Generally, port 27 is an aperture into recipient chamber 22. An alternate guide tube (not shown) may be included to form an extended port 27 such that a sample recovery or dispersal tool can easily migrate to port 27. A cover may be employed on port 27 such that contaminants from outside recipient chamber 22 do not pass through port 27 when samples are being added or removed from recipient chamber 22. In accordance with certain aspects of the present disclosure, if a guide tube is included in association with port 27, the guide tube is generally an adapter. For example, if the recovery/dispersal tool is a needle, then guide tube 27 preferably facilitates the coupling of the needle to port 27.

The Franz cell apparatuses 31 are designated to determine passive permeation A or photokinetic permeation B into and through eye tissues 23. The Franz cell has two chambers—the donor chamber 21 and the recipient chamber 22. Eye tissue 23 is placed between the two chambers and sealed into place and held between the two chambers by a clamp (not shown). The recipient chamber 22 is filled with an aqueous solution selected to allow for chemical analytical methods. The donor chamber 21 is filled with a drug in a pharmacologically acceptable formulation, as described herein. The recipient chamber 22 is constantly stirred by a magnetic stir bar 26. A portion of the recipient chamber is placed in a heat block 25 heated to a physiological temperature (about 35.5° C.). At various time points, samples are dawn from the side arm port 27 for purposes of chemical analysis.

The passive permeation cell A provides permeation flux rates though the scleral tissue. In the photokinetic Franz cell B, a selected LED 28 is partially submerged within the drug formulation 24 within the donor chamber 21. The LED is driven by an external pulse generator at a selected pulse rate and connected to the LED electrical connectors 29. The scleral tissue 23 is positioned in contact with and under the drug formulation 24. The drug formulation in contact with the tissue is illuminated by the light 30 generated by the LED 28.

The photokinetic transocular drug delivery methods described herein are useful for the therapeutic treatment of a variety of ocular disorders by delivering a wide variety of drugs of a large variety of molecular weight ranges into and through the scleral tissue of the patient. Ocular diseases and disorders suitable for therapeutic treatment with the methods and systems described herein include but are not limited to cancer, such as primary ocular lymphoma; diabetic retinopathy, including proliferative diabetic retinopathy (PDR); diabetic retinoblastoma; diabetic macular edema; macular degeneration, including "wet" (exudative) macular degeneration and age-related macular degeneration (AMD); intraocular edematous; uveitis, including posterior uveitis; inflammatory diseases; retinitis; glaucoma, including neovascular glaucoma; cicatrizing conjunctivitis; myasthemia gravis; macular edema; choroidal neovascularization; endophthalmitis; ocular toxoplasmosis; and proliferative vitreous retinopathy (PVR). In accordance with aspects of the present disclosure, the transocular drug delivery methods described herein are useful in the treatment of diabetic retinopathy, macular edema, and diabetic retinoblastoma. In accordance with further aspects of the present disclosure, the transocular photokinetic ocular drug delivery (PODD) methods and systems described herein are useful in the treatment of glaucoma, including neovascular glaucoma. In accordance with still further aspects of the present disclosure, the transocular photokinetic ocular drug delivery (PODD) methods and systems described herein are useful in the treatment of uveitis and ocular inflammatory diseases. In accordance with another aspect of the present disclosure, the transocular photokinetic ocular drug delivery (PODD) methods and systems described herein are useful in the treatment of macular degeneration, including both wet macular degeneration and age-related macular degeneration.

In accordance with the treatment of ocular disorders and diseases using the systems and methods described herein, the methods of treatment for any of the diseases and disorders set forth above, particularly glaucoma, diabetic retinopathy, uveitis, and macular degeneration, comprise administering a therapeutically effective amount of a compound, preferably a high-molecular weight compound, or a pharmaceutically acceptable salt, solvate, hydrate, racemate, or stereoisomer thereof, to a subject in need thereof using the PODD methods described herein. For example, the instant disclosure envisions methods for the treatment of glaucoma comprising administering a therapeutically effective amount of a compound, preferably a high-molecular weight compound, or a pharmaceutically acceptable salt, solvate, hydrate, racemate, or stereoisomer thereof, to a subject in need thereof. Similarly, the instant disclosure envisions methods for the treatment of uveitis, diabetic retinopathy, or macular degeneration in a patient wherein the method comprises administering a therapeutically effective amount of a compound, preferably a high-molecular weight compound, or a pharmaceutically acceptable salt, solvate, hydrate, racemate, or stereoisomer thereof, to a subject in need thereof using the PODD methods described herein. Further, the instant disclosure envisions methods for the treatment of VEGF-related angiogenic diseases, particularly those selected from the group consisting of cancer, age-related macular degeneration (AMD), and diabetic retinopathy, wherein the method comprises administering a therapeutically effective amount of a compound, preferably a high-molecular weight compound, or a pharmaceutically acceptable salt, solvate, hydrate, racemate, or stereoisomer thereof, to a subject in need thereof using the PODD methods described herein.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Methotexate Transcleral Delivery

Materials and Methods

A traditional "up and down" vertical Franz cell skin perfusion apparatus as described above was adapted and used for this sclera tissue permeation model. The absorption spectrum of the test drug, methotrexate (MTX, a drug used in the treatment of primary ocular lymphoma) was determined. Two wavelengths of light were selected of this facilitated permeation study. Samples of the Franz recipient solution were taken at 15, 30 and 60 minutes of photokinetic exposure and passive controls and analyzed by HPLC.

Instruments and Materials

Franz cells (PermeGear, Inc, Bethlehem Pa.) having an 11.28 mm diameter permeation area, 1.0 cm$^2$ were used in the MTX experiment. A photokinetic ocular drug delivery (PODD)-modified Franz cell testing device was configured so that it accommodated the placement of LEDs within the donor chamber. The cells were placed within an aluminum block heater 35.5° C. on a magnetic stir bar setup (Custom manufactured by PermeGear, Inc, Bethlehem Pa.).

Figure 7:
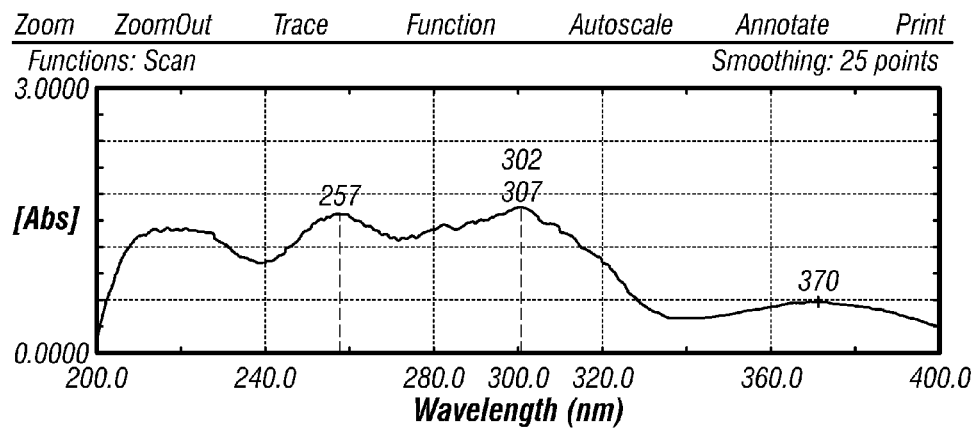
FIG. 7 illustrates a spectrophotometry light absorbance scan of methotrexate (MTX).

Spectrophotometry measurements (Beckman DU 650) of Methotrexate (Sigma Chemicals) (FIG. 7) showed a minor peak of absorption at 370 nm in the near visible light range.

Discrete wavelength LEDs were purchased from Roithner Lasertechnick GmbH, Vienna, Austria as follows: 351 nm, #RTL350-30; 370 nm, #RLS-UV370. Peak emitting wavelengths are ±10 nm at the 50% radiance output. The LEDs were driven by a square wave pulse generator built by the investigators for this study. The adjustable square wave pulse generator provided pulsed electrical energy set at 24 cycles per second (CPS) with a 50% pulse duration (ON 50%, OFF 50% of the time). Driver current to the LEDs was limited to or slightly below the manufacturers specified drive current level to avoid exogenous heat generation. The experimental arrangement is shown generally in FIG. 6. As shown therein, Franz cells 31 are adapted for sclera photokinetic permeation studies. A donor cell contains the test drug (in this example, methotrexate (MTX)) in a solvent formulation. The recipient cell is filled with a balance salt solution. Samples for chemical analysis are taken from the side arm 27 of the Franz apparatus as discussed above. Control cells are set up the same, but without the LED. LEDs are driven by a square wave pulse generator (not shown) at a voltage slightly less than the manufacture's specified voltage.

Sclera

Ovine sclera was used as the subject tissue, and was selected because ovine sclera is slightly thicker than human or pig sclera, and so the total drug flux may be less than what could be attained in human use. Ovine eyes were procured by enucleation within one hour after euthanasia and placed in tissue culture medium with antibiotics and antimycotics and refrigerated at 4° C. Sclera tissue was dissected from the eyes and placed between the donor and recipient chambers of the Franz apparatus. Sclera was stored for a maximum of 30 hours in the tissue culture at 4° C. before the start of the experiment.

Drug Formulation

Methotrexate (MTX; (4-Amino-10-methylfolic acid hydrate); available from Sigma-Aldrich Corp., St. Louis, Mo.) was dissolved in a permeation enhancement carrier of water, 30% propylene glycol, 5% Ethyl Lactate, 0.1% Azone, and 0.75% hyaluronic acid as a gelling agent, with 0.1% neolone 850 as a preservative. An infinite donor sink model was used wherein 0.75 grams of the drug formulation (1.875 mg of each) was placed in the Franz donor cells. Hanks isotonic salt solution served as the Franz recipient cell fluid.

HPLC Method

HPLC analysis was performed according to a method developed in our lab. Briefly, a Beckman Coulter system consisting of 125 pumps, 508 auto sampler and 168 diode array detector was used with an XTerra RP-C18, 150×40 mm, 3 μm column. The analytes were eluted with a gradient mobile phase from 25-30% Methanol in HPLC grade water with 0.1% Trifluoroacetic Acid (TFA) and flow rate of 0.7 ml/min. 32 Karat™ software (Beckman Coulter, Inc.) was used for acquisition of chromatograms.

Recipient Cell Concentration Method

The Franz recipient cell balanced salt solution was analyzed by the HPLC method for MTX concentration.

Histology

Sclera samples were taken and placed in formalin as follows: Normal control sclera with no exposure to drug or light, Franz cell 60 minute control drug only exposure and Franz cell 60 minute exposure to both drug and 350 nm LED light. Fixed slides were evaluated for structural integrity and gross appearance by a pathologist blinded as to the origin of the sample tissue.

Statistics

Statistical analysis was performed using one way analysis of variance (ANOVA) with Bonferroni's correction. Significance was accepted at $p<0.05$.

Results

Recovered MTX concentration from Franz cells experimental results are expressed as drug quantity per square centimeter (cm2) of exposed tissue over time, e.g., micrograms of MTX recovered from the Franz recipient cell per square centimeter of sclera at each time point ($\mu g/cm^2$/Time). The human eye volume is only about 6.5 mL, so the ratio of drug permeation surface available to the internal volume is very large compared to transdermal drug delivery applications. This surface to volume ratio indicates that photokinetic in vitro drug flux volumes attained can greatly exceed the required therapeutic range of the drugs tested, even with greater than 60 minutes of photokinetic exposure time.

Effect of Light Wavelength on Permeation

Figure 8:
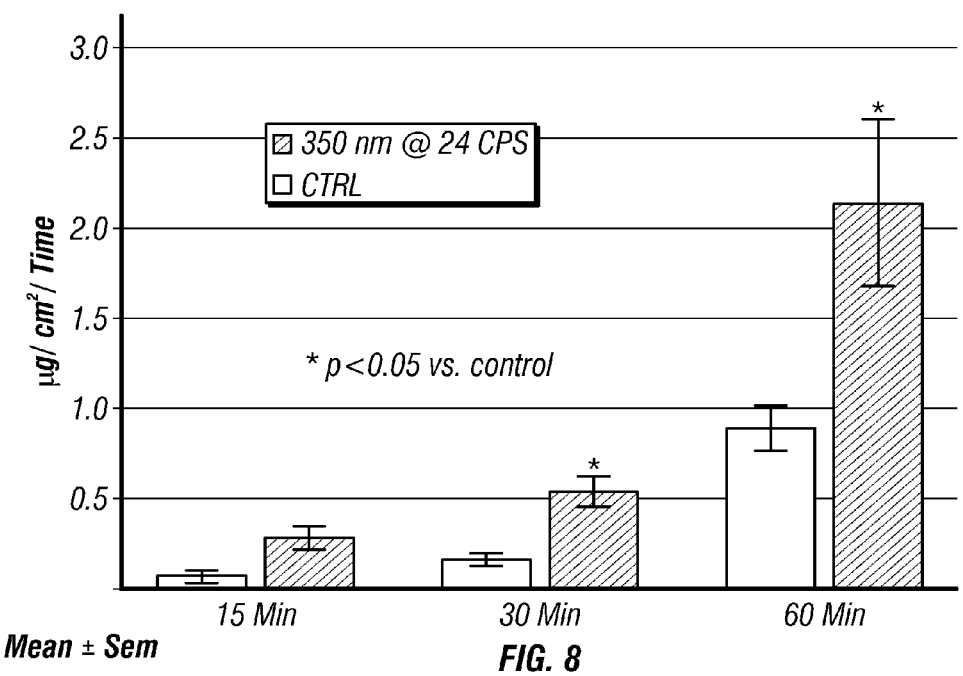
FIG. 8 illustrates MTX permeation PODD at 350 nm@24 CPS vs. passive permeation controls per $cm^2$ of sclera at 3 time points.
Figure 9:
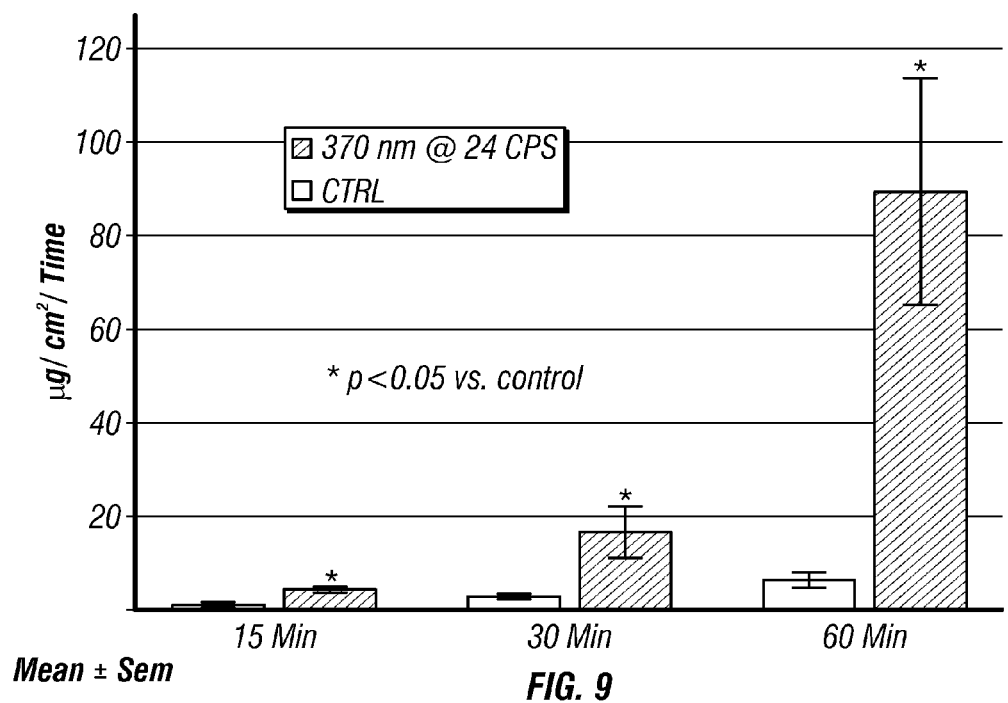
FIG. 9 illustrates MTX permeation PODD at 370 nm@24 CPS vs. passive permeation controls.

For both wavelengths of light tested all PODD cells showed an improvement of MTX permeation through the scleral tissue. In the 350 nm group, significant ($p<0.05$) levels of MTX were recovered at the 30 and 60 minute time points (FIG. 8). In the 370 nm group, significant ($p<0.05$) levels of MTX were recovered at the 15, 30 and 60 minute time points (FIG. 9). The 370 nm group showed a much higher flux rate at all time points when compared to the 350 nm group.

Histological Examination

Histological examination of the 60 minute PODD exposure compared to passive control revealed no differences between the samples. The fibrous layers in all samples were grossly intact. No zones of necrosis were found in the sclera sample areas immediately adjacent to the portion compressed by the Franz cell flange. The two Franz cell mounted sclera samples (60 minute passive control and the PODD) demonstrated no differences from the normal sclera not exposed to drug or light. The structural integrity of the sclera was observed to be grossly intact and undamaged.

Discussion

The data clearly shows that pulsed light of a specific wavelength may facilitate methotrexate (MTX) to permeate through ovine sclera at significantly higher flux rates when compared to passive controls. The sharp flux rate differences between the relatively narrow wavelengths selected (350 nm and 370 nm) for this study further suggests the system is highly wavelength dependent even within a narrow range.

The energy of light increases as the light wavelength decreases in size; 350 nm light has more energy than 370 nm light. The results demonstrate that light with a lower energy caused significantly higher permeation rates. Thus, high light energy in itself is not the deciding factor of permeation rates. The absence of sclera damage under histological examination from both light groups along with the differences in flux rates between within each of the test groups suggests that light energy did not cause unseen physical damage to the fibrous scleral layers that could result in permeation pathways. One would suspect that if there was a physical disruption of the sclera by the light itself, the higher energy 350 nm light would have higher flux rates. Additionally, incoherent near visible light at 350-370 nm as emitted from an LED has not been shown to cause physical damage or disruption to other tissues.

All electronic components generate heat when a current is applied. LEDs driven by excessive current will get hot and quickly burn out. When driven at or slightly below the specified current, exogenous heat is minimal. In early experiments, temperature increases within the Franz donor cell could not be detected, although we suspect a minor amount of heat is generated. Again, if heat from the LED was the mechanism of increased permeation, then the flux rate of both drugs should have been increased in all the wavelength groups.

The use of LEDs as the light source is of convenience. Light emitting diodes (LED) have inherent narrow wavelength emissions based on the composition of the diode material and are available in discrete wavelengths of emission and require no further optical filtering. LEDs can be rapidly cycled and switched on and off with no warm up or cool down light emission phase as in an incandescent bulb. They are very efficient in converting electrical energy to light energy and produce very little exogenous heat. The actual light emitting portion of a LED is quite small. The majority of the packaged LED is the housing/lens and electrical connections. Therefore, the small size, inherent narrow light wavelength of emission, and efficiency of light production per energy consumed makes the LED an ideal choice for this system especially for the limited area of the eye available. Other light sources could be used if properly optically filtered and controlled for rapid cycle operation.

Light pulse rate may affect the flux rate in the photokinetic system. Unpublished data from early work suggests that high pulse rates (in excess of 120 cps) actually diminish flux rates. The selection of the 24-100 cycles per second pulse rate is based on the inventor's prior data of extensive photokinetic transdermal Franz cell testing of various low molecular weight drugs, such as described in U.S. Pat. No. 7,458,982 B2.

The selection of Hanks balanced salt solution in the Franz recipient cell rather than HPLC grade water was necessary due to the ability of the sclera membrane to regulate osmolarity across this membrane.

Although the total MTX flux did not reach a therapeutic level of 400 μg in this first attempt, various strategies can be employed to increase flux rates across the sclera barrier membrane such as: optimization of drug carrier/chemical permeation enhancement, increasing the drug concentration in the topical formulation, increasing the exposure time of the drug on the membrane and increasing the exposed transport area.

Conclusion

The in vitro model demonstrates that pulsed incoherent light of a selected wavelength directed onto a solution of methotrexate applied to ovine sclera can be used to facilitate transscleral permeation. The transscleral flux rate in the PODD system appears to be wavelength dependent as determined by spectrophotometry absorption of a subject drug. The PODD system did not damage or alter the sclera exposed to light energy at the wavelengths and intensity used herein. The PODD system may be used as an alternative for needle injection into the eye.

Example 2

Delivery of Insulin

Two pertinent ocular drugs were selected for testing the hypotheses. Methotrexate (MW=454 Daltons) is used for the treatment of primary ocular lymphoma. Insulin (MW=5808 Daltons, 5.808 kDa) and insulin like growth factors have been implicated as a possible preventive treatment for diabetic retinopathy. The transscleral delivery of methotrexate has been described in Example 1, above.

A traditional "up and down" vertical Franz cell (11.28 mm diameter permeation area, 1.0 cm$^2$) perfusion apparatus (FIG. 6) was adapted and used for this sclera tissue permeation model. PODD modified Franz cell testing device was configured so that it accommodated the placement of the selected discreet wavelength LEDs within the donor chamber. Discrete LEDs at 351 nm and 370 nm were used for the MTX study and 405 nm and 450 nm for the insulin study (peak emitting wavelengths at ±10 nm at the 50% radiance output). The LEDs were driven by a square wave pulse generator set at 24 cycles per second (CPS) with a 50% pulse duration.

Ovine eyes were procured by enucleation within one hour after euthanasia and placed in tissue culture medium with antibiotics and antimycotics and refrigerated at 4° C. Sclera tissue was dissected from the eyes and placed between the donor and recipient chambers of the Franz apparatus within 30 hours of enucleation.

Insulin at a concentration of 200 IUs/mL was dissolved in a drug carrier comprised of water, 30% propylene glycol, 5% Ethyl Lactate, 0.1% Azone, 0.75% hyaluronic acid as a gelling agent with 0.1% neolone 850 as a preservative. 0.75 grams of the drug formulation was placed in the Franz donor cells. Hanks isotonic salt solution served as the Franz recipient cell fluid.

Samples of the Franz recipient solution were taken at 15, 30 and 60 minutes of photokinetic exposure and passive controls and analyzed by HPLC for MTX concentration and expressed as μg/cm$^2$/Time. Samples for insulin were taken at 24 hours and tested by ELISA methodology and expressed as microunits insulin/cm$^2$/24 hours. The experimental arrangement is shown in FIG. 6.

Normal control sclera with no exposure to drug or light, Franz cell 60 minute control drug only exposure and Franz cell 60 minute exposure to both drug and 350 nm LED light were taken and placed in formalin. Fixed slides were evaluated for structural integrity and gross appearance by a pathologist masked as to the origin of the sample tissue.

Results

Figure 10:
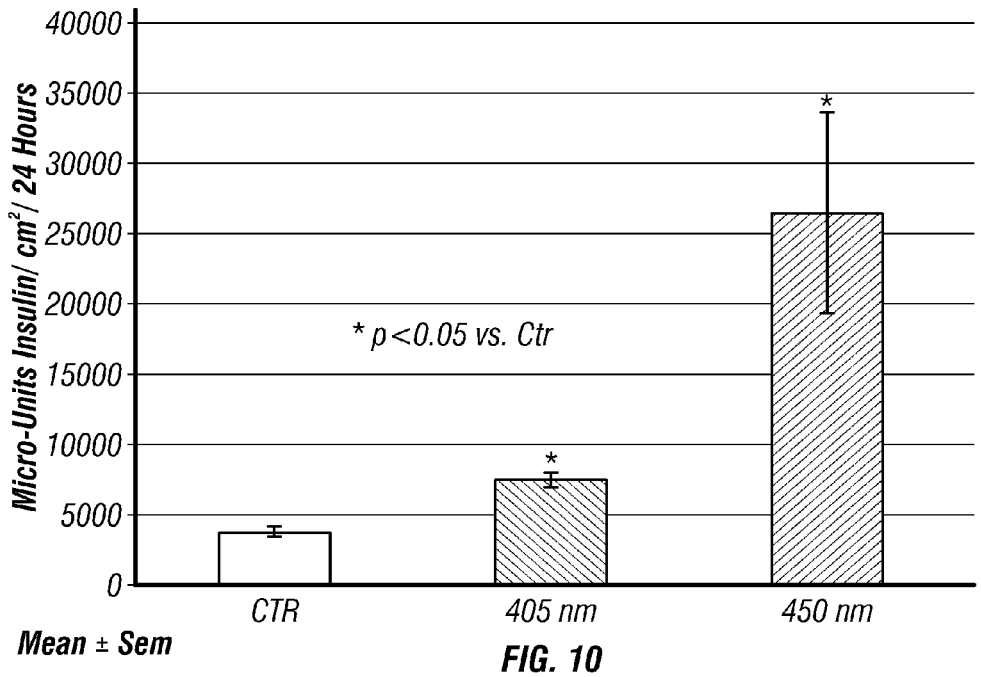
FIG. 10 illustrates PODD Insulin permeation at 405 and 450 nm vs. control for 24 hours at 24 CPS. Herein a 200 IU/mL mixture in a drug carrier solution was placed in the Franz donor cell. A large difference in permeation is noted here also even within a narrow range of light wavelength.
Figure 11:
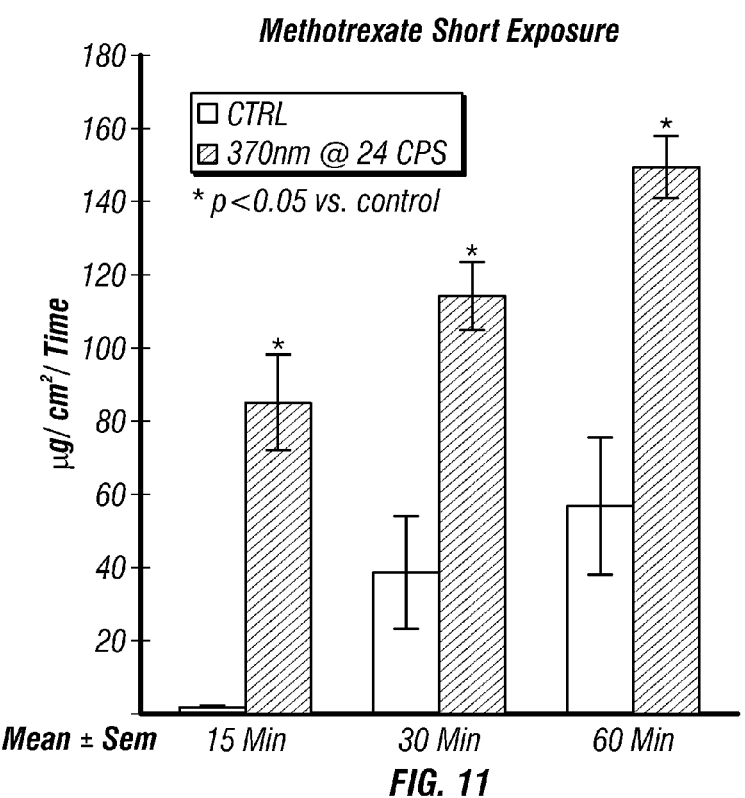
FIG. 11 illustrates MTX permeation PODD at 370 nm@24 CPS vs. passive permeation controls per $cm^2$ of sclera over a short (60 minute) exposure range.
Figure 12:
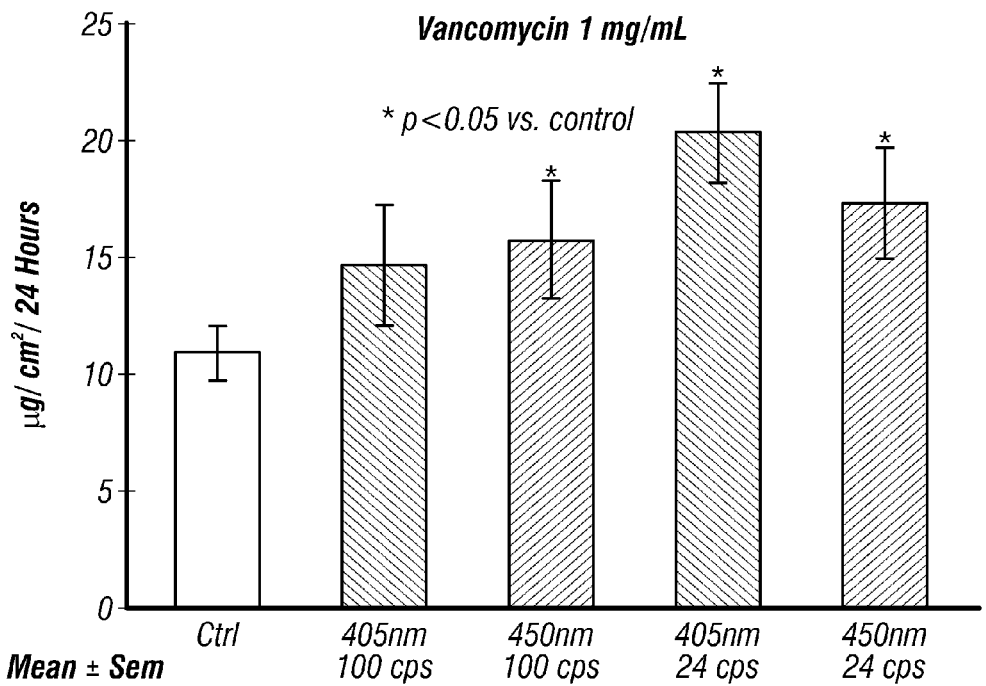
FIG. 12 illustrates the effect of a variety of wavelengths on permeating vancomycin through scleral tissue using PODD cells.
Figure 13:
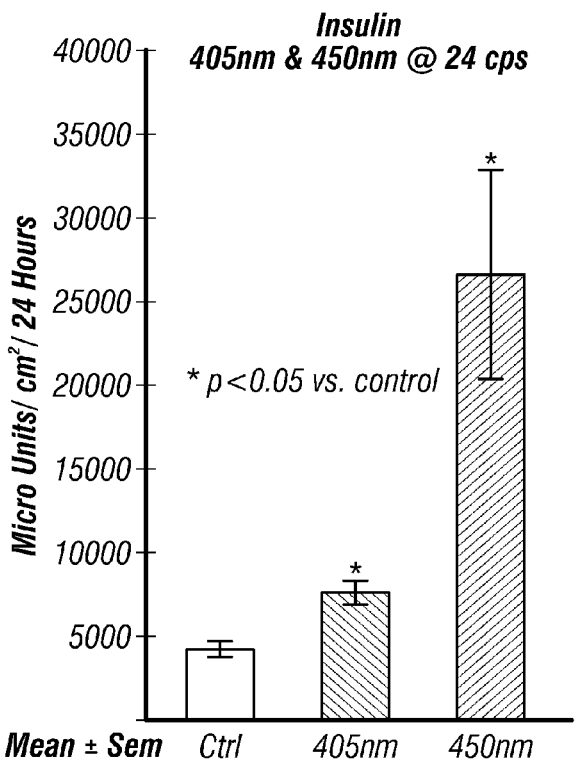
FIG. 13 illustrates the effect of 405 and 450 nm wavelength@24 CPS verses passive permeation controls on permeating insulin through scleral tissue using PODD cells.
Figure 14:
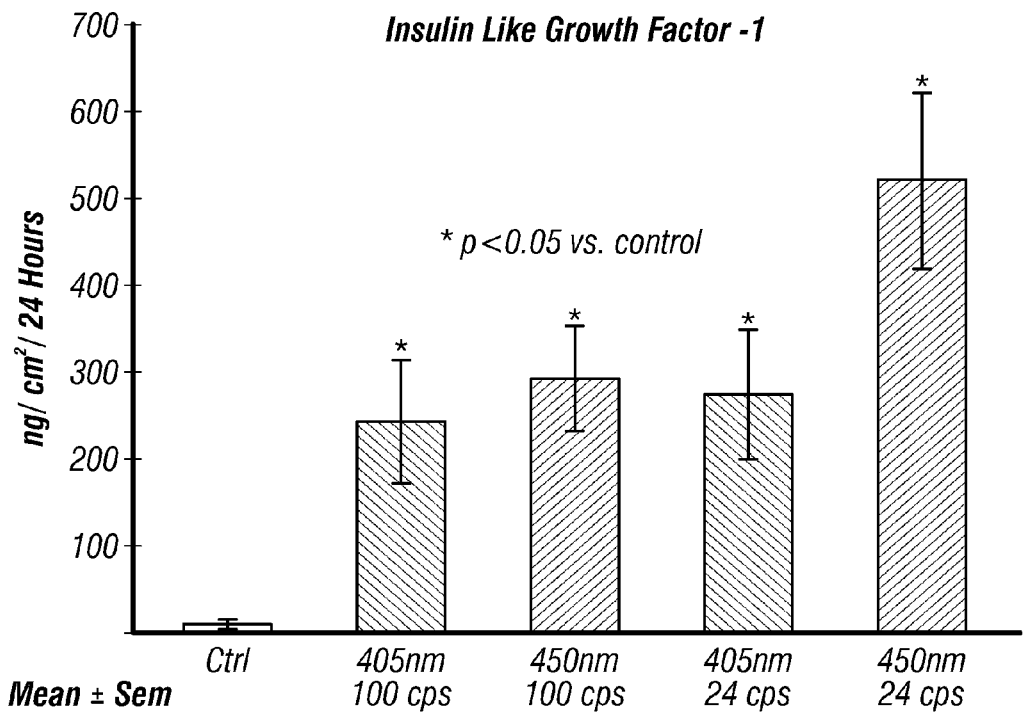
FIG. 14 illustrates the effect of 405 and 450 nm wavelength@24 CPS versus passive permeation controls on permeating insulin like growth factor 1 through scleral tissue using PODD cells.
Figure 15:
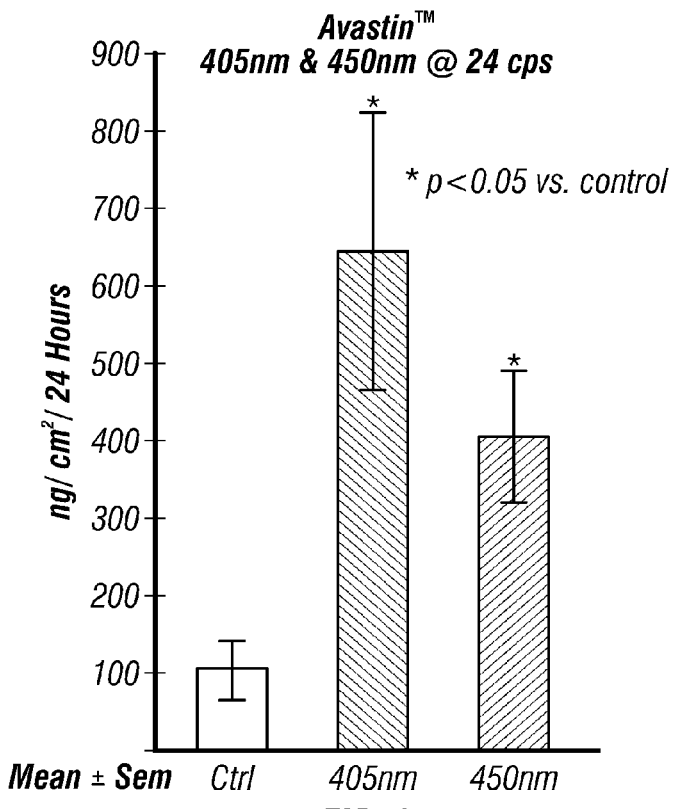
FIG. 15 illustrates the effect of 405 and 450 nm wavelength@24 CPS versus passive permeation controls on permeating Avastin™ through scleral tissue using PODD cells.
Figure 16:
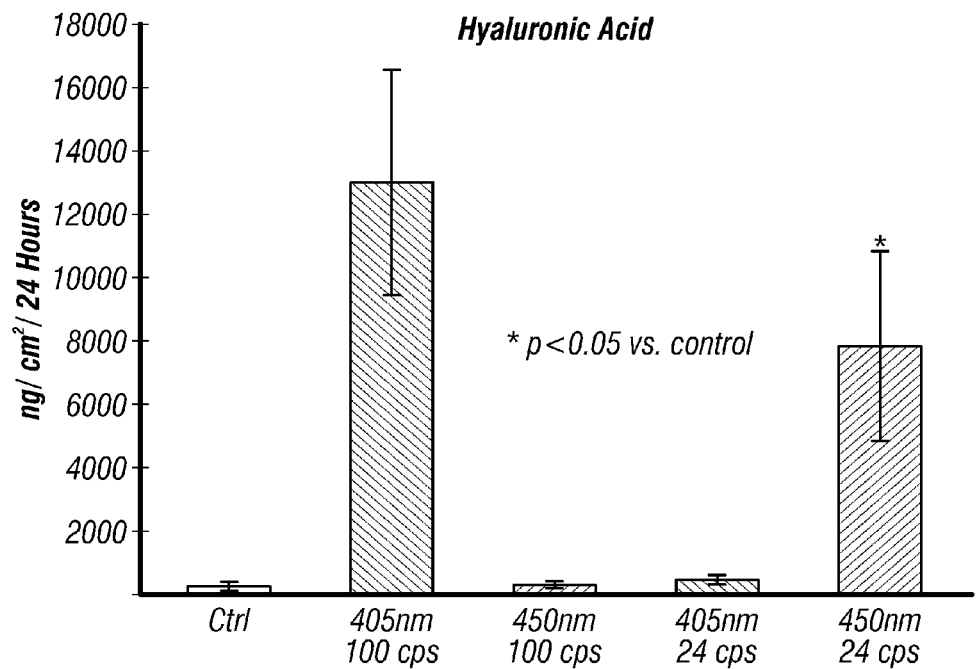
FIG. 16 illustrates the effect of 405 and 450 nm wavelength@24 CPS versus passive permeation controls on permeating hyaluronic acid (HA) through scleral tissue using PODD cells.

For both wavelengths of light tested in the insulin experiments, all PODD cells showed an improvement of insulin permeation through the scleral tissue vs. controls. In both light groups, significant ($p<0.05$) levels of insulin was recovered at the 24 hour time point (FIG. 10). The 450 nm PODD group showed 7 times higher flux rate while the 405 nm group showed a 2 times higher flux rate vs. controls. Histological examination of the 24 hour 405 nm PODD exposure compared to the passive control and normal sclera not exposed to drug or light revealed no differences between the samples. As was the case in the experiment with methotrexate, the structural integrity of the sclera was observed to be grossly intact and undamaged.

Discussion

The data clearly shows that pulsed light of a specific wavelength may facilitate insulin to permeate through ovine sclera at significantly higher flux rates when compared to passive controls. The sharp flux rate differences between the relatively narrow wavelengths selected (405 and 450 nm for insulin) for this study further suggests the system is highly wavelength dependent even within a narrow wavelength range.

The results demonstrate that light with a lower energy (370 nm vs. 350 nm and 450 nm vs. 405 nm) caused significantly higher permeation rates. Thus, high light energy in itself is not the deciding factor of permeation rates. The absence of sclera damage under histological examination from the insulin 405 nm light group along with the differences in flux rates between within each of the test groups suggests that light energy did not cause unseen physical damage to the fibrous scleral layers that could result in permeation pathways. Additionally, incoherent near visible light in the 405-450 nm visible range as emitted from an LED has not been shown to cause physical damage or disruption to other tissues at the emitting intensities and exposure times used herein.

The use of LEDs as the light source is of convenience. Light emitting diodes (LED) have inherent narrow wavelength emissions based on the composition of the diode material and are available in discrete wavelengths of emission and require no further optical filtering. LEDs can be rapidly cycled and switched on and off with no warm up or cool down light emission phase as in an incandescent bulb. They are very efficient in converting electrical energy to light energy and produce very little exogenous heat. The actual light emitting portion of a LED is about 300 microns square the remainder is packaging. Therefore, the small size, inherent narrow light wavelength of emission, and efficiency of light production per energy consumed makes the LED an ideal choice for this system especially for the available limited application area of the eye.

Various strategies can be employed to increase total flux rates across the sclera barrier membrane such as: optimization of drug carrier/chemical permeation enhancement, increasing the drug concentration in the topical formulation, increasing the exposure time of the drug on the membrane and increasing the exposed transport area. The available accessible sclera of a human eye is about 4-6 cm$^2$. Insulin and insulin like growth factor therapeutic dose requirements are likely to be very small but with frequent administrations.

Recent photokinetic transdermal permeation studies by the Applicants have demonstrated significant flux rates of high molecular weight hyaluronic acid (4500K Daltons) through intact human skin under similar photokinetic conditions. Scleral tissue is more permeable than human skin. The practical upper molecular weight limit with the PODD system is unknown and may be determined by the specific molecular configuration rather than molecular weight per se.

Conclusion

The in vitro model demonstrates that pulsed incoherent light of a selected wavelength directed onto a solution of methotrexate or insulin applied to ovine sclera can be used to facilitate transscleral permeation without damaging the scleral tissue or chemically altering the drug.

Example 3

Transcleral Insulin Delivery of High Molecular Weight Drugs

Figure 17:
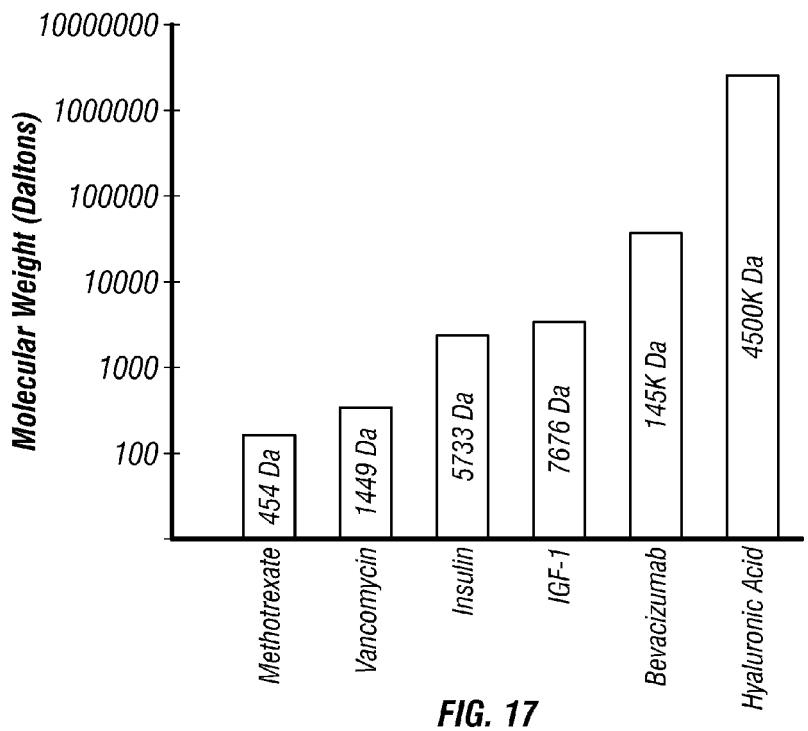
FIG. 17 illustrates a summary comparison of the size of biologically active materials which can be transsclerally/transcorneally applied using the procedures and apparatus of the present disclosure.

Using the same procedures as set out above, and the apparatus of FIG. 6, scleral tissue permeation determinations of methotrexate over a short time period, as well as the scleral tissue permeation of vancomycin (1 mg/mL), insulin, Insulin Like Growth Factor-1 (IGF-1), Avastin™ (bevacizumab; Genentech, San Francisco, Calif.), and hyaluronic acid (HA) were conducted. High molecular weight hyaluronic acid (4500 K Da in size) was selected as a test compound because the sodium salt of hyaluronic acid (SH) is a high molecular weight biopolymer made of repeating disaccharide units of glucuronic acid and N-acetyl-β-glucosamine, and which is present in the vitreous body and the aqueous humor. Hyaluronic acid is a natural polymer which, due to its water retaining capability, binds to cell membranes and can therefore be considered to be a putative vehicle for controlled ocular delivery (Durrani, et al., *Int. J. Pharm.*, Vol. 118 (2), p. 243-250 (1995)). The results are shown in FIGS. 11-16, and are summarized in FIG. 17. As can be seen from FIG. 17, significant transscleral flux is observed with molecules ranging from about 450 Daltons (methotrexate) to molecules with molecular weights of about 4500 K Da (hyaluronic acid, HA). In addition to the significant and therapeutic transscleral fluxes illustrated by the methods and apparatus of the present disclosure, the present photokinetic system significantly increases the intrascleral deposition of compounds as well. This in turn allows for the sclera itself to become a depot for extended drug release into the intravitreal space, as well as the eye circulation.

Example 4

Transcleral Insulin Delivery Rabbit Model

A proof-of-concept experiment was conducted for the PODD system of the present disclosure with a rabbit ocular drug delivery model using a fluorescent labeled human insulin molecule as the test drug for a 60-minute photokinetic exposure. Exogenous human insulin can be differentiated from the endogenous rabbit insulin; the human insulin FITC (fluorescein isothiocyanate) fluorescent tag further allows for tracking of the drug within the tissues. FITC-labeled human insulin (5733 Daltons in size, available from Invitrogen Corporation, Carlsbad, Calif. as insulin modified at the N-terminus of the B-chain with an FITC conjugate/tag) was used as a test drug for transocular applications, as the ELISA analytical methods are widely available and accepted to provide a quantitative as well as a functional assay for the molecule. Franz permeation cells as described herein were utilized to define functional photokinetic parameters of light wavelength and pulse rate in vitro prior to the animal study.

Figure 18A:
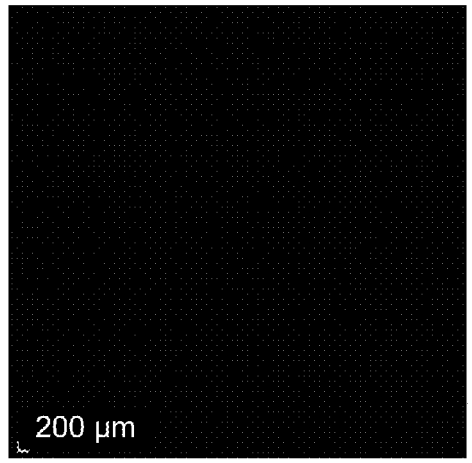
FIG. 18A-18C illustrate rabbit optic disc imaging results of fluorescent tagged human insulin administered with the PODD system of the present disclosure.
Figure 18B:
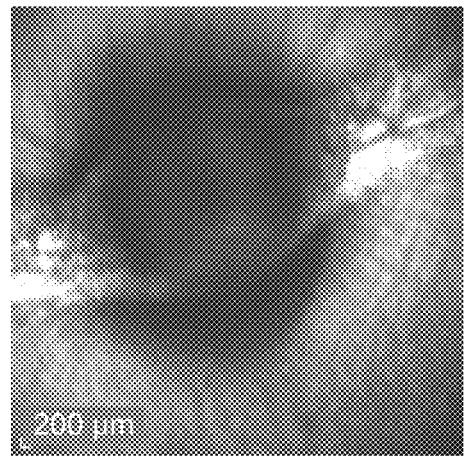
Figure 18C:
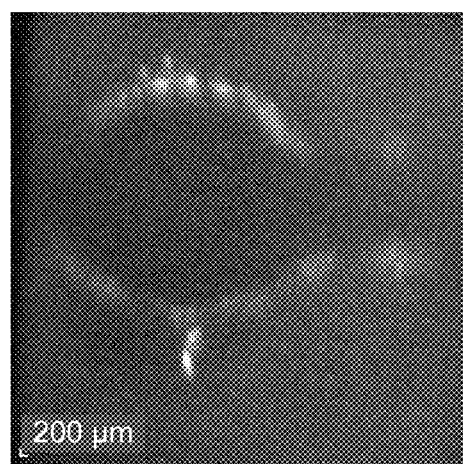
Figure 19A:
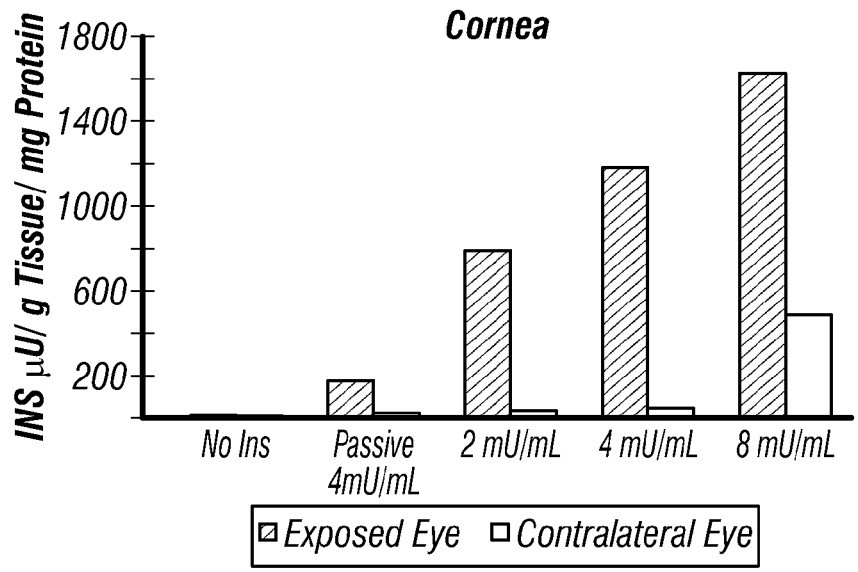
FIGS. 19 A-F illustrate three concentrations of human FITC labeled insulin used in the PODD device vs. passive permeation of 4 mU/mL in the various fluids and tissues of the rabbit eye (60 minute exposure).
Figure 19B:
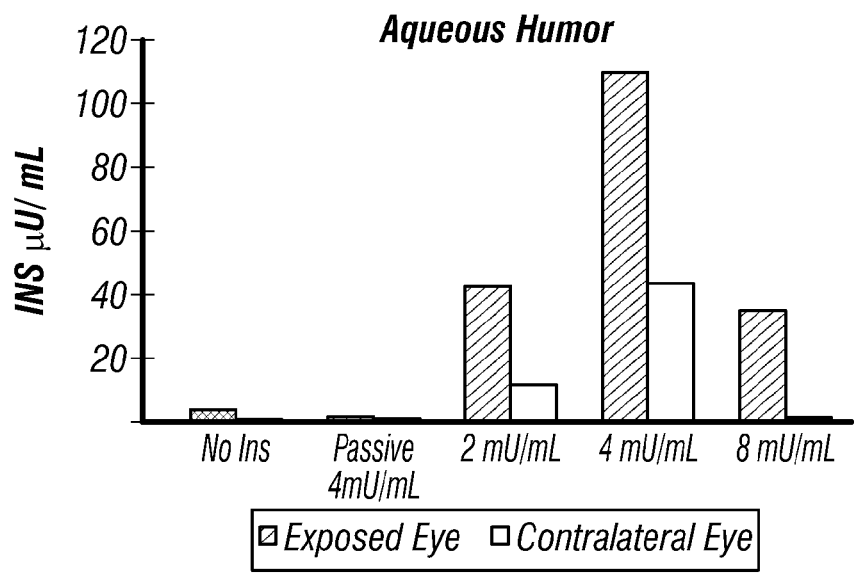
Figure 19C:
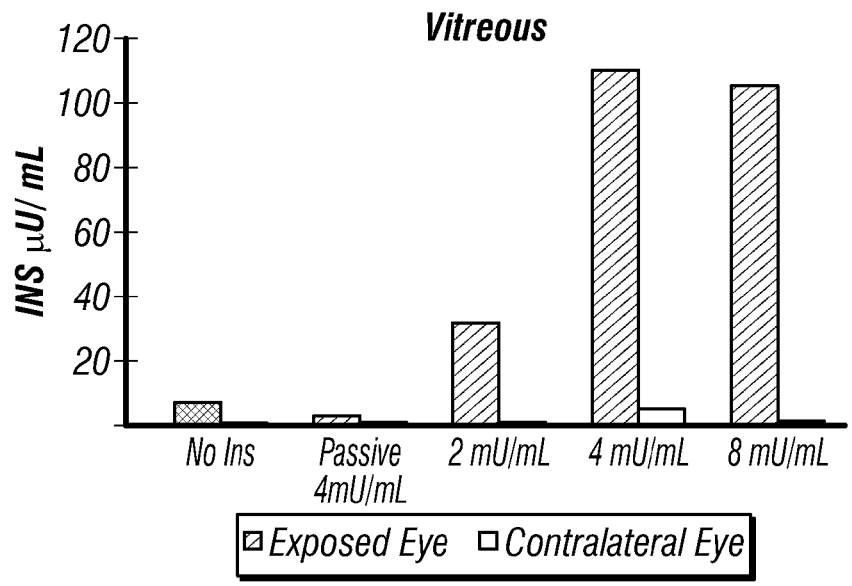
Figure 19D:
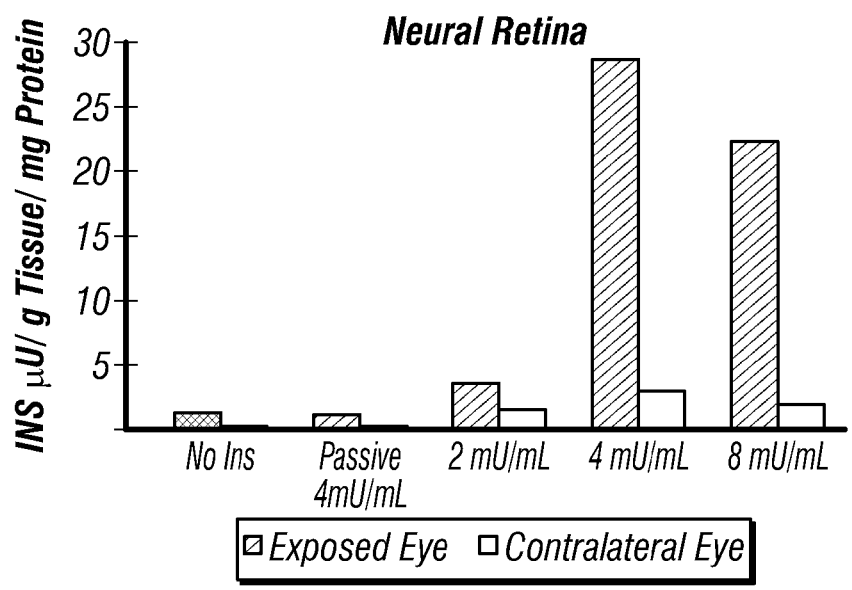
Figure 19E:
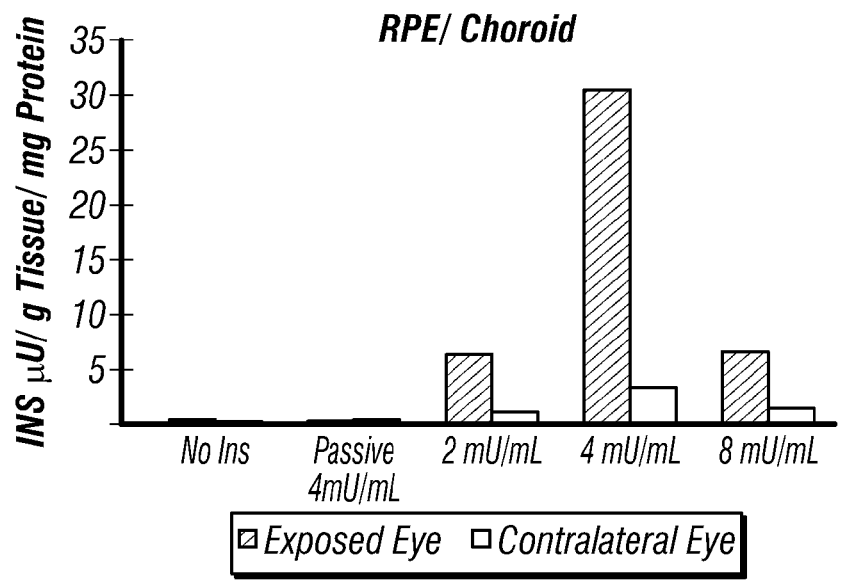
Figure 19F:
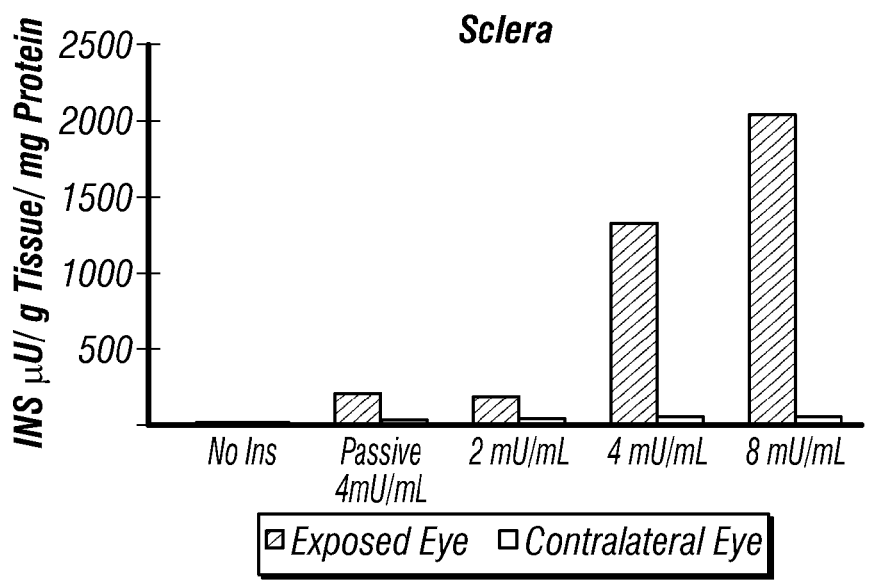

In this series, rabbits were fitted with transscleral photokinetic device, such as shown in FIG. 1 of this disclosure, for one hour. One eye of the test rabbit was exposed to the topically applied insulin, 4 micro-units/mL in a suitable drug carrier formulation under an adapted photokinetic device using 450 nm LED light pulsed at 100 CPS for one hour, applied to a 2 cm$^2$ area of sclera. Images were taken of the posterior optic disc, the area where the retina, optic nerve and blood vessels come together on the posterior segment of the eye. These results are shown in FIGS. 18A, 18B, and 18C, with FIG. 18A illustrating the fluorescence baseline image, FIG. 18B illustrating an IR baseline image, and FIG. 18C illustrating the fluorescence image after 1 hour of PODD. These rabbit optic disc images demonstrate that the fluorescent tagged human insulin administered with the PODD system of the present system reached the posterior segment of the rabbit's eye. The contralateral eye showed no fluorescence. Passive permeation in other rabbits with the same experimental setup did not show fluorescence in the optic disc.

After treatment for one hour with the transscleral photokinetic device described herein, and after the images in FIGS. 18A-18C were taken, the animals were sacrificed and tissues and fluids were taken for quantitative analysis. The tissues from the photokinetic exposed eye and the contralateral eye that were assayed for human insulin concentration. A passive permeation control animal without light exposure but under otherwise similar conditions was also assayed. The results of three concentration of human FITC labeled insulin in the PODD device vs. passive permeation of 4 mU/mL in the various fluids and tissues of the rabbit eye after 60 minute exposure are presented in FIGS. 19A-19F, and in Table 1, below. Although the ELISA analytical test method employed is specific for human insulin, there is some cross reactivity with rabbit insulin ("No Ins" in the Figures) as the kit contains rabbit proteins as preservatives. A small quantity of human insulin was also found in the untreated contralateral eye transferred by the blood circulation, as also evidenced in the figures.

TABLE 1

| | Insulin (µU/mL) | | Insulin (µU/gram Tissue/mg Protein) | | | |
|---|---|---|---|---|---|---|
| | Vitreous Humor | Aqueous Humor | Sclera | Cornea | RPE Coroid | Neural Retina |
| Photokinetic exposure | 118 | 114 | 1498 | 1500 | 31 | 28 |
| Photokinetic Contralateral | 6 | 40 | 98 | 22 | 3.75 | 2.5 |
| Passive Delivery | 4 | 2 | 200 | 200 | 0.89 | 1.3 |
| Passive Contralateral | 2 | 2 | 56 | 22 | 0.65 | 0.98 |

In view of the results shown in Table 1, this test demonstrated the feasibility of the photokinetic transscleral and/or transcorneal drug delivery system as described herein. The photokinetic transscleral delivery provided drug concentrations within the several ocular compartments.

Other and further embodiments utilizing one or more aspects of the inventions described above can be devised without departing from the spirit of Applicant's invention. Further, the various methods and embodiments of the disclosure can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A device for photokinetic transscleral ocular drug delivery, the device comprising:
   a generator that provides an oscillating electrical pulse in electrical communication with at least one light emitting diode (LED) that is mounted on a photokinetic patch adapted and dimensioned to be inserted under an eyelid and fit against an external ocular surface of an eye of a patient, the photokinetic patch including a drug layer, wherein the at least one LED receives the oscillating electrical pulse and responds by providing an incoherent light directed through the drug layer and towards an interior of the eye of the patient at a wavelength selected to induce a photokinetic transocular translocation of a drug loaded in the drug layer.

2. The device according to claim 1, wherein the generator is a repeat cycle square wave pulse generator.

3. The device according to claim 1, wherein the photokinetic patch further comprises a light pad that includes the at least one LED.

4. The device according to claim 3, wherein the light pad is comprised of an optically clear material.

5. The device according to claim 4, wherein the optically clear material is poly(methylmethacrylate) or silicone rubber.

6. The device according to claim 1, wherein the at least one LED is a discrete wavelength LED characterized by a peak emitting wavelength at a 50% radiance output that is ±10 nm of the wavelengths selected from the group consisting of 350 nm, 370 nm, 390 nm, 405 nm and 450 nm.

7. The device according to claim 1, wherein the drug layer comprises a biologically active substance and a solvent.

8. The device according to claim 7, wherein the drug layer further comprises at least one gelling agent.

9. The device according to claim 8, wherein the at least one gelling agent is selected from one or more of hydroxyethyl cellulose, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols, and tyloxapol.

10. The device according to claim 7, wherein the biologically active substance is selected from one or more anesthetics, anti-infectives, antibiotics, antifungals, antivirals, antineoplastics, anti-VEGFs, antineovasculars, steroids, anti-inflammatories (including NSAIDS), immunomodulators, gases, antioxidants, nanoparticles, genes, cytokines, peptides, antithrombotics, nucleotides, RNAs, anti-compliment medications, compliment modulating medications, peptides, immunoglobulins, antibodies, antigens, anti-glaucoma medications, hormones, vitamins, amino acids, silicone liquids, heavy liquid tamponades, cellular nutrients, anti-apoptotic agents, anticoagulants, tissue adhesives, cofactors, coenzymes, enzymes and combinations thereof.

11. The device according to claim 1, wherein the at least one LED emits light at a wavelength from about 350 nm to about 700 nm.

12. The device according to claim 1, wherein the at least one LED is an infrared light emitting diode (ILED).

13. The device according to claim 3, wherein the light pad is coated on at least one surface with a reflective coating or layer.

14. The device according to claim 1, wherein the generator is a pulse generator that induces delivery of pulsed incoherent light.

15. The device according to claim 14, wherein the pulsed incoherent light is at a pulse rate between 1.7 cycles per second (cps) and 120 cps.

16. The device according to claim 14, wherein the pulsed incoherent light is applied at a duty cycle between 50% and 75%.

17. The device according to claim 1, wherein the generator is adapted and configured for mounting on an ear of the patient proximate to the external ocular surface.

18. The device according to claim 1, wherein the generator is mounted on a headband that is adapted and dimensioned to be fit over a head of the patient undergoing the photokinetic transscleral ocular drug delivery.

19. The device according to claim 1, wherein the device is supplied with the drug layer preloaded with the drug.

20. The device according to claim 1, wherein the drug layer is loaded with the drug at the time the photokinetic patch is inserted onto and fit against the external ocular surface of the patient.

21. The device according to claim 1, wherein the drug layer is loaded with a large molecule drug having a molecular weight of over 10,000 Daltons.

22. The device according to claim 1, wherein the drug layer is loaded with a large molecule drug having a molecular weight of over 100,000 Daltons.

\* \* \* \* \*